United States Patent [19]

Manahan, Sr.

[11] Patent Number: 5,165,287
[45] Date of Patent: Nov. 24, 1992

[54] DETERMINING FRACTURE MODE TRANSITION BEHAVIOR OF SOLID MATERIALS USING MINIATURE SPECIMENS

[75] Inventor: Michael P. Manahan, Sr., State College, Pa.

[73] Assignee: Battelle Columbus Division, Columbus, Ohio

[21] Appl. No.: 477,641

[22] Filed: Feb. 9, 1990

[51] Int. Cl.⁵ .............................................. G01N 3/20
[52] U.S. Cl. ........................................ 73/851; 73/826
[58] Field of Search ................... 73/826, 851, 12, 788, 73/789, 794, 795, 799, 845, 844

[56] References Cited

U.S. PATENT DOCUMENTS 4,864,867  9/1989  Manahan, Sr. ........................ 73/851

Primary Examiner—Jerry W. Myracle
Attorney, Agent, or Firm—Watkins, Dunbar and Pollick

[57] ABSTRACT

A method of determining fracture mode transition behavior (FMTB) of solid materials by using stress field modified miniature specimens. The method is an improvement in the method of determining mechanical behavior information from specimens only so large as to have at least a volume or smallest dimension sufficient to satisfy continuum behavior in all directions. FMTB of the material is determined from the measurements taken during the loading of the specimen resulting in the formation of cracks and/or the further propagation of cracks in the miniature specimen and/or fracture. The specimens are provided with grooves that induce additional stress field modifying stress components in the specimens during the test. These additional stress components result in a desired stress state in the specimens which could not be achieved otherwise. The methods are useful in determining FMTB for the material, when the specimen thickness is smaller than previously thought necessary for valid FMTB determinations.

14 Claims, 18 Drawing Sheets

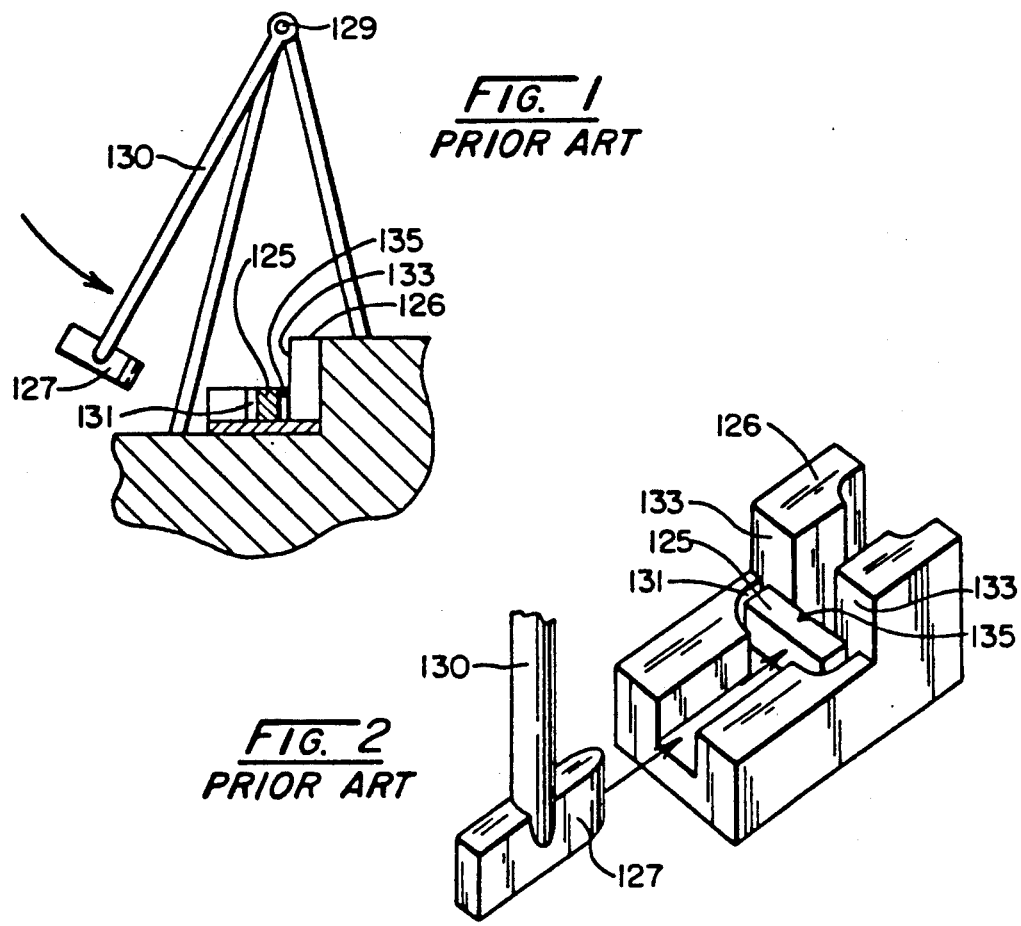
FIG. 1 PRIOR ART
FIG. 2 PRIOR ART
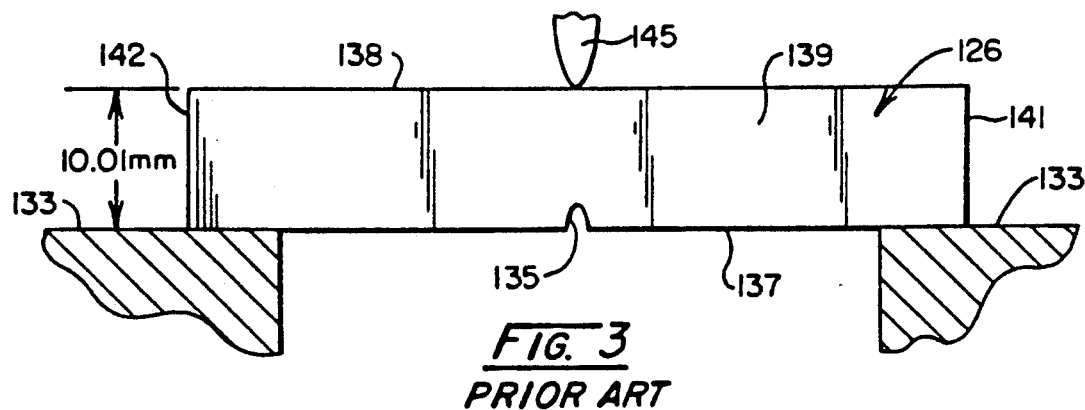
FIG. 3 PRIOR ART
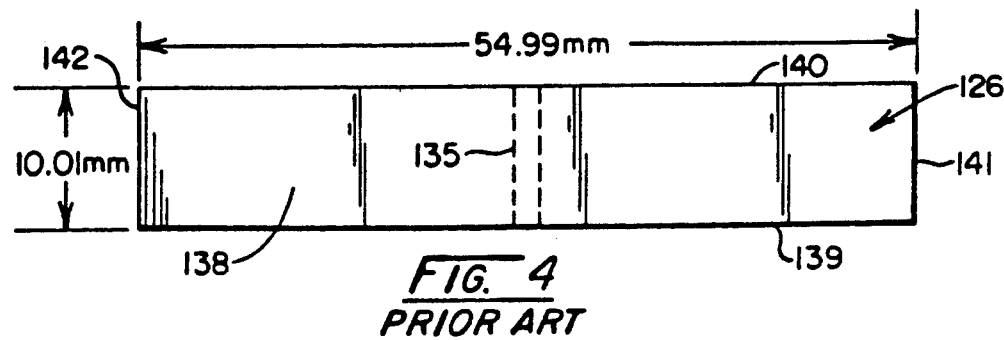
FIG. 4 PRIOR ART

DETERMINING FRACTURE MODE TRANSITION BEHAVIOR OF SOLID MATERIALS USING MINIATURE SPECIMENS

FIELD OF INVENTION

This invention relates to methods and apparatus for determining the mechanical behavior of solid materials and is especially useful for determining and measuring the mechanical materials when loaded or stressed for the purpose of establishing the design, use, safelife, and post-service criteria of the material. Although the term miniature is relative, as are all size descriptive terms, it is a fair characterization to define the field of this invention as the determination of the mechanical behavior of materials from miniature specimens, i.e., specimens noticeably smaller than prior conventional specimens in the materials testing field. More particularly, this invention relates to the testing of material specimens of thickness and size less than thought necessary for valid determinations of fracture mode transition behavior (FMTB), such as ductile-brittle transition temperature (DBTT) of solid materials, including but not limited to ferritic steels.

BACKGROUND OF THE INVENTION

Determination of the mechanical behavior physical properties of materials is necessary so that materials may be selected for use, evaluated when in use, and evaluated after use. From these determinations, decisions are made as to which materials to use, the conditions under which they can be used, and whether such materials in use can be continued to be used with safety. These types of determinations are particularly useful for determining the effects of environmental loading such as nuclear radiation on the mechanical properties of in-service materials. This invention is fully applicable to the determination of mechanical behavior of such materials but is also applicable to materials not subjected to radiation and the validity of the invention was demonstrated for materials not subjected to radiation.

The prior art includes U.S. Pat. No. 4,567,774 having the inventor, Michael P. Manahan, common with this application, and assigned to the same assignee. This earlier patent, hereinafter referred to as the "prior patent", includes the basic concepts upon which this invention is based. The disclosure of the prior patent is included herein by reference and the portions of that disclosure not specifically needed for the disclosure of this improvement invention are not included herein. However, reference to the prior patent may be helpful to the understanding hereof.

In the past, the most common procedure has been to determine the mechanical behavior of materials by testing large samples that are either created more or less simultaneously or side by side with the product that is intended to be used or are cut from the same batch of material. In the determination of the mechanical behavior of solid materials and particularly metals, the practice is to make tensile, fatigue, creep, stress relaxation, ductile/brittle transition behavior, fracture toughness, etc. specimens; and these are then subjected to loads while measurements are taken of the force, time, displacement, temperature, energy, velocity, crack length, etc. of the specimen. Information on stress and strain which can be thought of as normalized load and deflection respectively as well as other useful parameters are then obtained by simple mathematical operations. For example, in a uniaxial tensile test the stress is determined by dividing the measured load by the specimen cross sectional area.

While this may be satisfactory in most instances, there are other circumstances such as the post-irradiation testing of materials used in nuclear reactors where samples may be unavailable in sufficient size and quantity to carry out these destructive tests during the life of the materials in use. In general, neutron irradiation space for materials investigations is limited and costly. It is, therefore, desirable to use specimens of minimum volume. Since neutron irradiation costs scale with specimen volume, miniaturized mechanical behavior testing can provide significant savings in irradiation testing costs for nuclear materials investigations. In addition, it is possible to provide mechanical behavior information which is not ordinarily obtainable due to space limitations in irradiation experiments and thus expedite alloy development investigations. Of course, miniature specimen testing is applicable to materials investigations for other nuclear technologies as well as non-nuclear technologies requiring mechanical behavior characterizations from a small volume of material. One such non-nuclear application is cutting small pieces of material from in-service components and using miniature specimens to measure the current mechanical behavior state. These data can then be used to estimate the remaining life of the in-service component.

Alternatively, a miniaturized bend test can be employed wherein the fracture mode transition behavior for the material is determined by suspending the specimen between two spaced apart points while simultaneously bringing down a substantially centrally-positioned punch onto the notched and/or precracked specimen to deflect it and by providing other modifications to the specimen to achieve reasonably flat fracture surface and sufficient constraint so that fracture mode transitional behavior can be measured. This type of test can be characterized as a three point bend test. The present invention was conceived as a solution to the problem of determining the fracture mode transition behavior from miniature specimens which are thinner and smaller in volume than those conventionally employed in the art. More particularly, this invention relates to the testing of material specimens of thickness less than thought necessary for valid determinations of ductile-brittle transition temperatures (DBTT) particularly, and less than the minimum size as taught by ASTM A370-77, E23-86, and E812-81.

There are four principal conceptual innovative aspects to the miniaturized fracture mode transition behavior (FMTB) testing method of this invention. The first is the use of specimens that are significantly thinner and smaller than those currently in use. The second is the use of an experimental stress field modifying technique so that useful data can be obtained using small specimens. A particular manifestation is application of a transverse load in the thickness direction and/or making side grooves and spacing them such that a nearly constant through thickness stress field of sufficient magnitude so as to yield useful data is achieved. The third is the use of conceived and verified analysis techniques to produce results that have significant, adequate, and useful correlation with the results that are obtained by specified ASTM testing methods such as ASTM E23-86. The fourth is the use of the finite element method to calculate the direction and amount of additional load and/or side grooving to be applied to achieve the desired stress state in the specimen. In a particular manifestation, the finite element code is used to determine the amount of side grooving to achieve sufficient transverse tensile stress such that a reasonably flat fracture surface can be obtained.

This invention improves upon the method of U.S. Pat. No. 4,567,774 by teaching the modifying of the stress field during the testing with the miniature specimen. This modifying of the stress field can be done mechanically, or by using a force field such as a magnetic field in order to produce stresses in preferred orientations in the material, or by causing a change in the stress field conditions by the means of the removal of material on the sides of the specimen. Since plane strain need not be achieved in fracture mode transition behavior testing, side notching of the specimen is the preferred approach since this is experimentally less complicated. The material is removed in the form of a groove or crack on each side of specimen. In essence, the stress field modification replaces the need for material thickness.

In one particularly usefully test configuration, the miniature specimen is loaded in a three point bend test and parameters such as load, deflection, temperature, and time are measured. The data are then analyzed using either fracture appearance as the correlation parameter, or percent post-maximum energy as the new parameter. The data analysis process using this new parameter is necessary in order to obtain conventional full size energy vs temperature Charpy data as described in ASTM E23 using the miniature specimen data.

In essence, the stress field modification replaces the need for material thickness. The stress field is modified by providing grooves on two sides opposite to the notch to provide overlapping stress fields that include transverse stress components.

Current test procedures require a minimum specimen thickness which cannot be satisfied in many cases. This serves to preclude use of miniature specimens. The advantage of the present invention is that specimens which are much smaller than those currently in use can be accurately tested. This enables testing of materials removed from in-service components in cases where it is not possible to remove enough material to meet current ASTM test requirements. The invention can also be used to provide additional nuclear pressure vessel surveillance data by cutting miniature specimens from the broken halves of full size charpy specimens. Another advantage of the method of the invention is that the method allows the modifying of the stress field such that mixed mode fraction in the transition region can be avoided or conservatively accounted for. The invention enables restricting fracture in the stress region to fixed mode fracture.

Another advantage of the present invention is that in-service stress fields can be simulated in the laboratory thereby providing data which is more representative of component performance.

This invention enables the determination of the DBTT of materials from miniature specimens; i.e. specimens noticeably smaller than prior conventional specimens in the materials testing field. More particularly, this invention relates to the testing of material specimens of a size, approximately one twentieth by volume more or less than thought necessary for valid determination of ductile-brittle transition temperature (DBTT) of solid material determined using Charpy specimens.

SUMMARY OF THE INVENTION

In summary, this invention is a process of determining the mechanical behavior of solid materials, comprising: (a) providing a specimen of the material having a volume and smallest dimension sufficient to establish continuum behavior in all directions, and with a volume not more than $10^7$ times said sufficient volume, said specimen having a notch on one side to provide a stress concentration to initiate cracking; (b) modifying the stress field of the specimen by providing grooves on the two sides opposite to the notch to provide overlapping stress fields including transverse stress components which are approximately equal throughout the thickness, resulting in measurable fracture transition mode behavior; or (c) modifying the stress field of the specimen mechanically by providing a force in the transverse direction or by using a force field such as a magnetic field in order to produce stresses in preferred orientations in the material; (d) deforming the specimen by applying a load on the specimen in a direction different than the orientation of the modified stress field load or stress field component from side grooves; (e) measuring at least one key variable in step (d); and (f) determining the behavior of the material from the measurements taken according to the principles of the finite element method and/or the principles of linear or nonlinear material mechanics or both.

This invention is directed to solving the specimen size effects problem in FMTB testing. The invention enables the use of specimens which are much smaller than those currently in use. As specimen thickness is reduced, the transverse stress component decreases and the stress field near the crack tip changes from plane strain (triaxial state of stress) to plane stress (predominantly biaxial state of stress). Eventually a thickness and size is reached where the specimen plastic deformation is excessive and a reasonably flat fracture surface cannot be achieved and therefore the data can not be analyzed in a meaningful manner. Also, FMTB can not be measured.

Therefore, the invention uses side-grooves to increase the transverse stress, provide constraint, and enable the measurement of FMTB at specimen sizes where it would not be possible otherwise. In the prior fracture toughness testing art, side grooving is employed with large specimens for two basic reasons. The first is to keep a crack propagating in a desired plane and the second is to flatten the through thickness stress field in thick fracture toughness specimens so that relatively flat crack fronts are achieved. In this invention, side grooves are used for the first time in FMTB testing for the purpose of inducing a fairly uniform transverse stress field by reducing the specimen thickness or diameter to an optimum level so the stress field from the two notches overlap. This approach enables determination of FMTB in specimens which are thinner than required to obtain reasonably flat fracture surfaces which can be accurately analyzed.

Further, this invention provides a method of data analysis which enables accurate correlation between miniature FMTB specimens and full size ASTM E23 specimens such as the Charpy specimen. The new parameter needed is the percent post-maximum energy. The fracture surfaces are studied to determining the proper post-maximum energy index to be used for analysis of the miniature FMTB data to correlate with conventional Charpy data.

A particular object of this invention is to provide a method of determining the DBTT of solid materials from specimens with only sufficient volume and smallest dimension to satisfy continuum behavior in all directions. It is a feature of this invention to provide a method of determining the DBTT of solid materials accurately by bending or tensile loading miniature specimens. Still a further feature is to determine the DBTT accurately by the finite element method, particularly to which a modified stress field has been applied along with the miniature bend test.

Another feature is to determine the mechanical behavior by the processes of continuum material mechanics carried out by a code which is applied according to a predetermined algorithm which has been determined to be statistically accurate.

An overall object of the invention is to provide the capability of determining mechanical behavior of material through a process using specimen sizes so small that they may be trepanned from existing structures without significantly altering the overall characteristics of the structures.

The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art, without departing from the scope or sacrificing any of the advantages of the invention.

BRIEF DESCRIPTION OF THE DRAWINGS

FIG. 1 is a schematic elevational view of one of the fixtures and specimens employed in the standard ASTM FMTB impact (Charpy) test used to determine ductile-brittle transition temperature (DBTT).

FIG. 2 is a schematic enlarged perspective view of the hammer, anvil, and specimen support portion of the apparatus shown in FIG. 1.

FIG. 3 is an elevational view of one of the fracture mode transition behavior specimens (Charpy V notch specimen) specified for use in ASTM E23-82, showing its position on the anvil.

FIG. 4 is a plan view of the specimen shown in FIG. 3.

Figure 5:
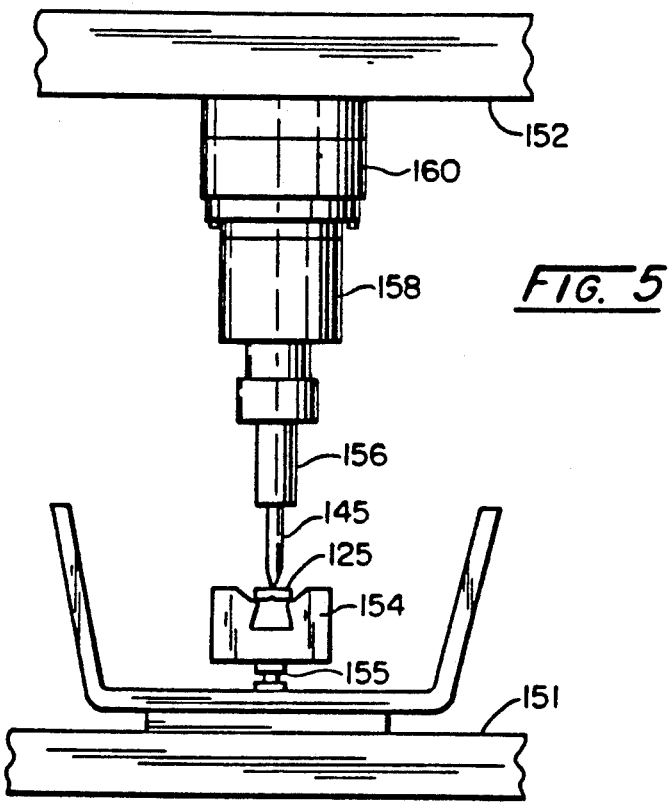
FIG. 5 is an elevation view of the apparatus used to test specimens of the configuration shown in FIGS. 3 and 4; as well as the specimen shown in FIGS. 6 and 7 by the method of this invention.
Figure 6:
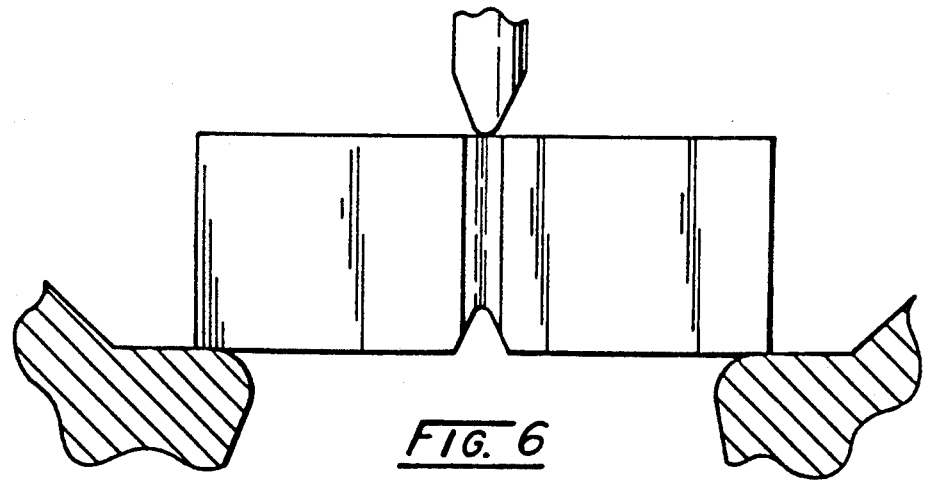
FIG. 6 is an elevational view of a specimen used in the test methods of this invention.
Figure 7:
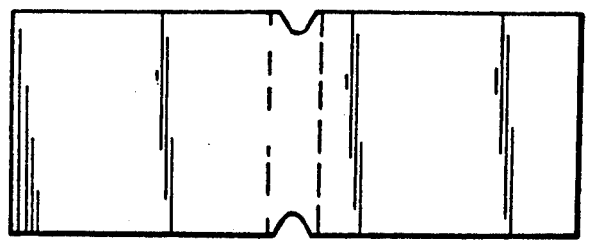
FIG. 7 is a plan view of the specimen shown in FIG. 6.

DETAILED DESCRIPTION OF THE INVENTION AND BEST MODE FOR CARRYING OUT THE PREFERRED EMBODIMENT

Referring to FIGS. 1 and 2, prior art ASTM methods and apparatus are shown for determining the FMTB of solid material in which the specimen is placed in an anvil 126 and struck by a hammer 127. The hammer 127 is suspended on an arm 130 that rotates on a trunion axis 129. The anvil 126 is provided with a receptacle 131 to receive the specimen 125 positioned against ledge faces 133.

Figure 13:
FIG. 13 is an elevational edge view of a punch used in the standard ASTM test for specimens in methods to determine DBTT.
Figure 14:
FIG. 14 is an elevational view of the edge of the punch used in the method of this invention to determine DBTT of material by the use of miniature specimens.

As most clearly seen in FIGS. 3 and 4 the specimen 125 is provided with a notch 135 on one elongated side 130. In the ASTM specification E23-82, dimensions shown in FIGS. 3 and 4 are specified. The shape is also specified and comprises two pairs of elongated parallel sides including a bottom 137 and a top 138 with sides 139 and 140. Square ends 141 and 142 are parallel to each other. Punch 145 is positioned intermediate the ends 141 and 142 on the top side 138 and has a configuration most clearly shown in FIG. 13.

Referring to FIG. 5, a different apparatus for determining FMTB 150 includes a fixed platen 151 and a movable platen 152 with the specimen 125 mounted between. The specimen is mounted on an anvil support 154 that is supported on platen 151 by an adjustable threaded member 155. A punch 145 is mounted in an adaptor 156 that is connected to a load cell 158 with a support 160 that is fastened to the upper movable crosshead 152. The apparatus 150 is used to provide a bend test to fracture which is used as another method embodiment in determining DBTT. In operation the movable platen 152 is lowered bending the specimen 125 and fracturing the bottom side 137 at the notch 135.

Figure 8:
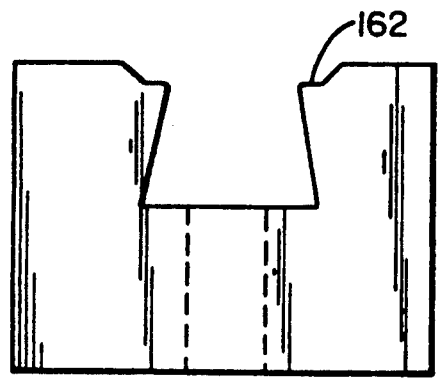
FIG. 8 is an elevational view of the standard ASTM anvil used in the test apparatus of FIGS. 1 and 2.
Figure 9:
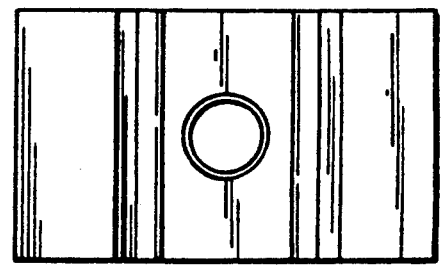
FIG. 9 is a plan view of the anvil shown in FIG. 8.
Figure 10:
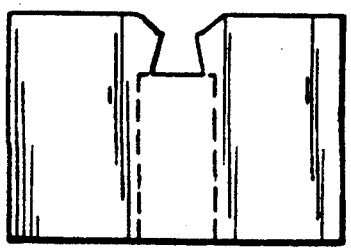
FIG. 10 is an elevational view of the anvil block used for bend testing miniature specimens in accordance with the methods of this invention.
Figure 11:
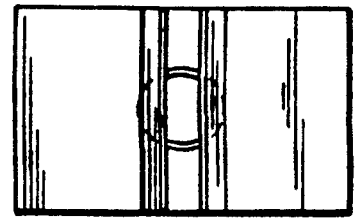
FIG. 11 is a plan view of the anvil shown in FIG. 10.
Figure 12:
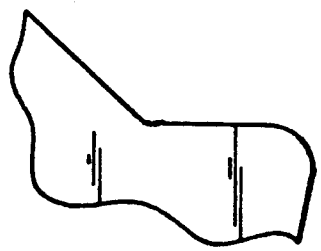
FIG. 12 is an enlarged view of the supporting specimen ledge surface in the apparatus shown in FIG. 10.

As seen in FIGS. 8 and 9 the dimensions and proportions and configuration of the anvil 154 provide ledges 162 on opposite sides to support the specimen 125 near the ends 141, 142 (see FIG. 3).

In the preferred embodiment, miniaturized FMTB three point bend specimens are tested to obtain ductile-brittle fracture transition information. Standard-size Charpy V notch (CVN) bars were also tested to provide a comparison with the miniature specimens. Table III.1 compares the miniature specimen dimensions with those of the conventional ASTM Charpy specimen. The Specimens are shown in FIGS. 3, 4, 6, and 7.

The smaller thickness of the miniature specimen results in a lower transverse stress field than that present in a standard CVN specimen. It is important to consider the effects of several variables such as notch acuity, strain-rate, and the size effect on the experimental results to be able to interpret them. While it is relatively easy to take strain-rate effects into account by means of a temperature translation in the energy temperature curves, the treatment of notch acuity and size effects is less straightforward. As stated in the prior art, there is a change in the fracture initiation micromechanism from microvoid coalescence to intergranular fracture as the notch root radius increases beyond a certain critical value. It is therefore important to be certain, in comparing the results of standard and miniature tests, that the basic mechanisms of deformation and fracture are comparable.

TABLE III.1

COMPARISON OF CONVENTION ASTM CHARPY SPECIMEN WITH MINIATURE SPECIMEN [MANA85]

| | ASTM | | | |
|---|---|---|---|---|
| | Charpy (mm) | Specim (in) | Mini (mm) | Specim (in) |
| Thickness (B) (Crack Plane) | 10.01 | (0.394) | 4.83 | (0.190) |
| Depth (H) direction of crack propagation | 10.01 | (0.394) | 4.83 | (0.190) |
| Length (L) | 54.99 | (2.165) | 12.70 | (0.500) |
| Reduced Side Thickness B | n/a | (n/a) | 3.86 | (0.152) |
| Notch Depth (a) 25 | 2.01 | (0.079) | 0.97 | (0.038) |
| Notch-Root Radius(r) | 0.25 | (0.010) | 0.25 | (0.010) |

The steel tested is a reactor-grade ASTM A508 steel, designated TSE-6,. For the purposes of simulating irradiation-induced embrittlement, different heat treatments were applied to the steel, to produce three different degrees of temperem-brittlement.

The miniature FMTB specimens were conceived on the basis of: microstructure and desired stress state. The lower bound on the minimum specimen dimension is dictated by the size of the largest microstructural inhomogeneity. This steel was found to have carbon-rich regions about 0.25 mm(0.010 in) and 0.5 mm (0.020 in) apart. For the specimens to be representative of the general behavior of the steel, the crack plane must be, at a minimum, 3 to 5 mm (0.12 to 0.20 in) or 5 to 10 times the characteristic inhomogeneity dimension.

The miniature FMTB tests can be performed at any experimentally achievable loading rate by varying the punch velocity. The miniature FMTB tests reported herein were of the notched-bar three-point bend type and were performed at static (slow-bend) loading rates. Standard Charpy v-notch specimens were tested dynamically and in slow bend on an anvil designed to conform to ASTM E23, which is the standard for notched-bar impact testing (See FIGS. 8 and 9). Procedures relating to test temperatures, alignment accuracy, and machining tolerances were followed. Table III.2 shows the relevant anvil support and punch dimensions, and the anvil and support are shown in FIG. 10, 11, 12, 13, and 14.

TABLE III.2

RELEVANT ANVIL SUPPORT AND PUNCH DIMENSIONS

| | Conventional Charpy Test [ASTM81] | | Miniature Specimen Test | |
|---|---|---|---|---|
| | (mm) | (in) | (mm) | (in) |
| Punch | 8.00 | (0.315) | 0.64 | (0.025) |

TABLE III.2-continued

| | RELEVANT ANVIL SUPPORT AND PUNCH DIMENSIONS | | | |
|---|---|---|---|---|
| | Conventional Charpy Test [ASTM81] | | Miniature Specimen Test | |
| | (mm) | (in) | | |
| Radius Punch Tip Width | 3.99 | (0.157) | 1.27 | (0.050) |
| Anvil Radius | 1.00 | (0.039) | 0.13 | (0.005) |
| Anvil Spacing | 40.00 | (1.575) | 11.68 | (0.460) |

Note: Both Anvils wre fabricated from Viscount 44 steel. The punch was made of Vega steel, Rockwell 60 hardness.

Figure 29:
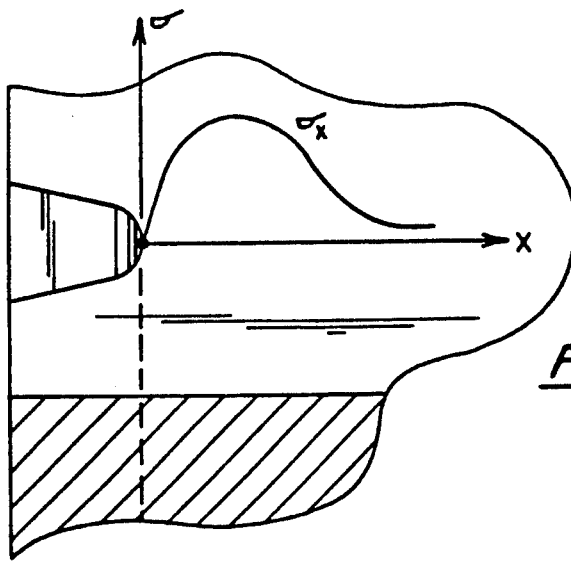
FIG. 29 is a schematic representation of the transverse tensile stress field component created at the notch when a specimen is loaded in the manner required for FMTB testing.
Figure 30:
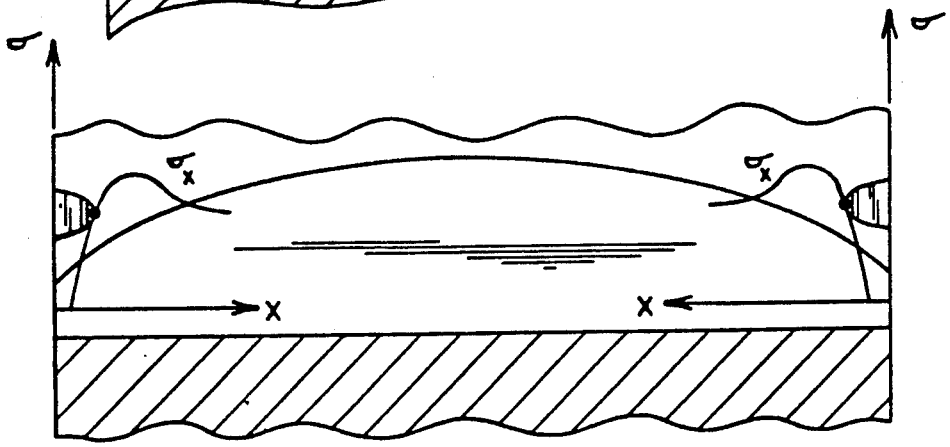
FIG. 30 is a schematic representation of the transverse tensile stress field component across the width of an ASTM standard size fracture toughness specimen when a specimen is loaded.
Figure 31:
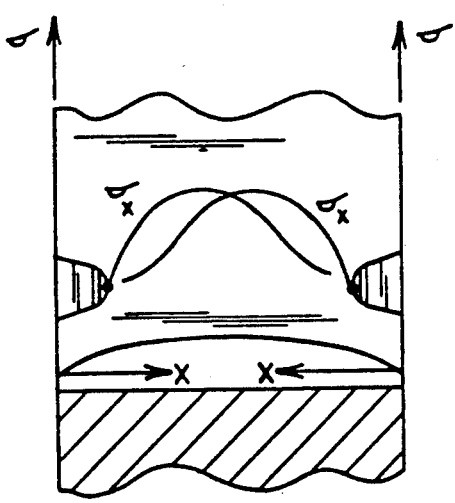
FIG. 31 is a schematic representation of the transverse tensile stress field component showing the through thickness stress field when a grooved miniature specimen is loaded in the manner required for FMTB testing.
Figure 32:
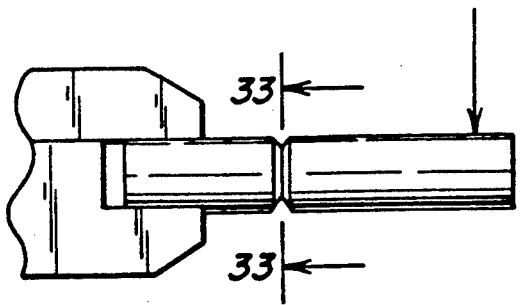
FIG. 32 is a side view of another embodiment of the specimen useful in the practice of this invention.
Figure 33:
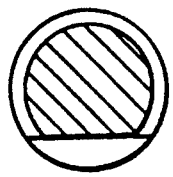
FIG. 33 is a cross sectional view of the embodiment shown in FIG. 32.
Figure 34:
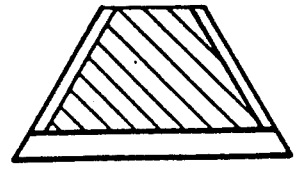
FIG. 34 is an end view of a specimen having a trapezoidal cross section for use in another embodiment of this invention.

As the specimen thickness decreases, the stress field close to the notch becomes less triaxial (plane-strain) and more biaxial (plane-stress). It is possible to modify specimen design to increase constraint. The approach used was to introduce side-grooves into the miniature specimens. The side-grooves introduce a transverse tensile stress field which acts to increase the through-thickness stress near the notch, thus helping to increase the triaxiality in the vicinity of the notch. The specimen thickness was reduced such that the side groove stress fields overlap and results in a significant through thickness stress field. While it is not possible to achieve plane strain conditions at most test temperatures, sufficient constraint is added so that fracture transition behavior can be measured. The through thickness component of stress for a notch is shown schematically in FIG. 29. The decrease of the through thickness stress field due to plastic constraint is shown schematically in FIGS. 30 and 31. The concept of bringing the side grooves into near proximity to modify the transverse stress in a miniature FMTB specimen is shown in FIG. 31.

Stress-field modification characterization may be accomplished using analytical methods such as finite-element analysis. Alternatively the effect of side-grooving and miniaturization on the stress state (and therefore on the fracture behavior) of the miniature specimens can be investigated by experimentation. Miniature specimens with different side-groove dimensions (depth and root radii) were tested at room temperature and using the same material (60R-93). Table III.4 gives a list of the various side-groove dimensions used in testing.

TABLE III.4

SIDE-GROOVING STUDY

| Miniature Specimen Identifying Numbers | | | | | | |
|---|---|---|---|---|---|---|
| 8a | 3 | 4 | 5 | 6a | 7 | 2 |
| Pre-Maximum Load Energy (kJ/m²) | | | | | | |
| 971.18 | 918.11 | 843.26 | 804.41 | 767.46 | 735.24 | 668.92 |
| Side-Groove Depth (mm) | | | | | | |
| 0.0 | 0.24 | 0.24 | 0.24 | 0.49 | 0.49 | 0.49 |
| Side-Groove Root Radius (mm) | | | | | | |
| n/a | 0.25 | 0.13 | 0.04 | 0.25 | 0.25 | 0.04 |
| Notch Root Radius (mm) | | | | | | |
| 0.25 | 0.25 | 0.25 | 0.25 | 0.13 | 0.04 | 0.25 |

All of the side-grooving tests were performed on the miniature 60R-93 specimens at room temperature (68' F.). None of the tests resulted in any brittle fracture. However, it was observed that pre-maximum load energy, obtained prior to major specimen deformation, could yield information on crack-initiation processes. The pre-maximum load energies showed a regular increase as the depth of the side-grooves decreased. The specimen without side-grooves (8a) exhibited the highest pre-maximum load energy. Among specimens with the same side-groove depth, there is a weaker correlation with side-groove root radius. Thus in specimens 3, 4 and 5, the pre-maximum load energy decreases as the side groove root radius decreases. Among the remaining specimens (6a, 7, 2), all with deep side grooves (0.49 mm), the sensitivity to side-groove root radius or notch root radius is less apparent. Table III.4 gives the various notch and side-groove dimensions as a function of decreasing pre-maximum load energy.

An important finding was that the specimens without side-grooves developed crack planes which did not stay parallel to the plane normal to the specimen length. None of the specimens with side-grooves exhibited this behavior. A conclusion to be drawn is that side-grooves are essential to testing miniature FMTB specimens, the constraint introduced by side grooving is sufficient to measure transition behavior.

The main findings of the side-grooving study are:
(1) Side-grooves are necessary to keep the crack propagation direction approximately in the plane normal to the specimen length. The specimens without side-grooves showed crack planes which did not follow the straight line from the notch to the punch.
(2) Crack-initiation energy is dependent on specimen geometry and the side-groove dimensions. The pre-maximum load energy was found to decrease with increasing side-groove depth and decreasing side-groove root radius.
(3) Since side-grooving changes the stress field at the ends of the notch, there could be an effect on the crack front, and hence on fracture appearance.

As described earlier, three heat treatments were applied to the ASTM A508 steel made, each resulting in a different temper-embrittlement. The materials were designated as:
60R-93 for Heat Treatment 6 [Tempered at 613° C. (1135 F.) for 4 hours, furnace-cooled]
5A-91 for Heat Treatment 5A [Tempered at 679° C. (1254 F.) for 4 hours, furnace-cooled]
60RR-5 for Heat Treatment 6R [Tempered at 705° C.(1301 F.) for 4 hours, furnace-cooled]

These are in order of increasing toughness. The 60R-93 material showed the most brittle behavior while the 60RR-5 exhibited the least.

Several parameters of interest can be extracted from bend test load-deflection curves, such as:
(a) Total absorbed energy to fracture
(b) Energies associated with crack initiation and propagation
(c) Yield load
(d) Maximum load
(e) Fracture load
(f) Deflection at brittle fracture Energies are obtained from the load/deflection curves by integration (i.e., by measuring the areas under the curves). A planimeter can be used for this purpose. With static testing the punch displacement velocity is constant, and it is not necessary to make corrections for the slowing-down of the striker as in impact testing.

Fracture-appearance measurements can be made from photographs of the broken surfaces of the specimens and/or by observation of the actual fracture surfaces under a stereomicroscope. Percent areas of fibrous (ductile) and cleavage (brittle) fracture are measured from magnified photographs by means of a planimeter. Fibrous or ductile fracture areas are identified by their dull, "torn" appearance; while brittle or cleavage-type fracture areas have a shiny, "faceted" appearance. Other fracture appearance features noted are shear-lips, which have a fibrous appearance.

An important aspect of the fracture appearance is the shape of the crack front. The conventional Charpy specimens exhibit a convex crack front when viewed with the notch closest to the observer. This indicates that the crack initiates near the center of the notch where the stresses are highest. The miniature specimens show a concave crack front, suggesting that crack initiation occurs near the side grooves. The presence of the side-grooves in the miniature specimens results in an increase in the stress level near the side grooves, and the stress may be high enough to initiate the crack in this region of the specimen. The prior art states that these differences in crack front shape indicate that the appearance of the full-width crack at the notch root does not necessarily coincide with maximum load. This can be assumed to be the case or the crack formation can be measured by a technique such as electricpotential (EP). The assumption is particularly valid near the lower shelf, which is one region of interest for conventional Charpy testing.

Small notched specimens exhibit greater plasticity due to lack of material (thickness) constraint. The miniature specimen geometry is modified by machining side grooves into the specimens and adjusting the specimen thickness with the objective of increasing the transverse stress component to approach a higher degree of triaxiality of the stress field near the notch. This technique induces cleavage, mixed mode, and ductile fracture in the miniature specimens at temperatures readily achievable in the laboratory, and produces relatively flat fracture surfaces. A temperature correction is applied to obtain conventional FMTB and, in particular, Charpy data.

It is recognized that the amount of transverse constraint achieved in the miniature specimens by the side grooving technique is arbitrary. Plane-strain conditions are not in general achieved except perhaps at very low temperatures, and the stress field in the vicinity of the notch is different in the miniature and conventional specimens. However, the degree of constraint achieved is enough to obtain a ductile-brittle transition.

The miniature test results are used to obtain an estimate of the Charpy 30 ft-lb dynamic transition temperature. The absorbed energy can be normalized by the crack plane area and used as the Charpy parameter. The 41 Joule (30 ft-lb) Charpy index used to define the transition temperature is normalized by the same factor, i.e., by the crack plane area. This results in a normalized Charpy index ob 512 kJ/m². To allow a direct comparison between the heats, all the test temperatures for the slow-bend tests are adjusted by subtracting the appropriate conventional Charpy impact transition temperature. These impact transition temperatures are given in Table IV.1. Using the 512 kJ/m² level as an index for both specimen sizes enables correction factors to be established to account for specimen size and loading rate for both the miniature and the standard CVN data.

TABLE IV.1

CONVENTIONAL CHARPY IMPACT TRANSITION TEMPERATURES

| Material | Temperature (C.) | (F.) |
|---|---|---|
| 60R-93 | 40 | (104) |
| 5A-91 | −7 | (19) |
| 60RR-5 | −29 | (−20) |

The superposition of data that results from this procedure establishes the rate-effect correction factor in the 41-J transition temperature at 45.3° C. Thus, there is a downward shift of 45.3° C. in the 41-J DBTT in going from dynamic to static test conditions for conventional CVNs. Following the same procedure for the miniature specimens results in a downward shift of 122° C. in going from dynamically tested conventional CVNs to statically tested miniature CVNs. Since 45.3° C. of this shift is due to the rate effect, the remaining 76.7° C. is attributed to the size effect in going from conventional to miniature specimens in slow-bend.

While the energy normalization approach yields reasonable data, it is not known to what extent the fracture mechanism exhibited by the miniature specimens are always representative of the standard CVNs. It is essential that the fracture mechanisms or modes be similar in both sizes of specimen for the 512 kJ/m² index or any other index. Of general concern is the increased ductility exhibited by miniature specimens, and the extent to which this is remedied by the presence of the side grooves. Investigation of the normalized energy parameter and the 512 kJ/m² index revealed that they are not, in general, correct for correlating miniature FMTB and conventional Charpy data. This is described below.

It is necessary to determine whether the fracture mechanism is the same for the 512 kJ/m² index in both standard and miniature specimens. Only in this case would the 76.7° C. size effect correction have a physical meaning.

Therefore fracture appearance was used as a direct measure of the validity of parameters to characterize the ductile-brittle transition. It was recognized that this parameter is valid regardless of specimen size, and that a quantitative measure of the ductile-brittle transition could be obtained if accurate measurement techniques are used. The ASTM Standard E-23 for Charpy impact testing gives four optional techniques for measuring fracture appearance: (1) a table can be used to convert linear measurements of the fracture surface areas to percent shear; (2) the appearance of the fracture surface may be compared with a pictorial chart of fracture appearance; (3) the fracture surface may be magnified and compared to a precalibrated overlay chart; or (4) magnified photographs may be measured by means of a planimeter.

The first three of these methods do not give very accurate estimates of the percent shear. Magnified photographs of the fracture surfaces can be measured by means of a planimeter, in conjunction with observations of the actual specimens under a steroscope to obtain good accuracy.

Fracture appearance is not generally used as a measure of the ductile-brittle transition due to the subjective nature of the usual methods of measurement, and to the fact that it requires considerable effort to obtain accurate data. Several industries, such as the nuclear industry, require by codes and standards the measurement of Charpy impact energy vs. temperature data.

Figure 15:
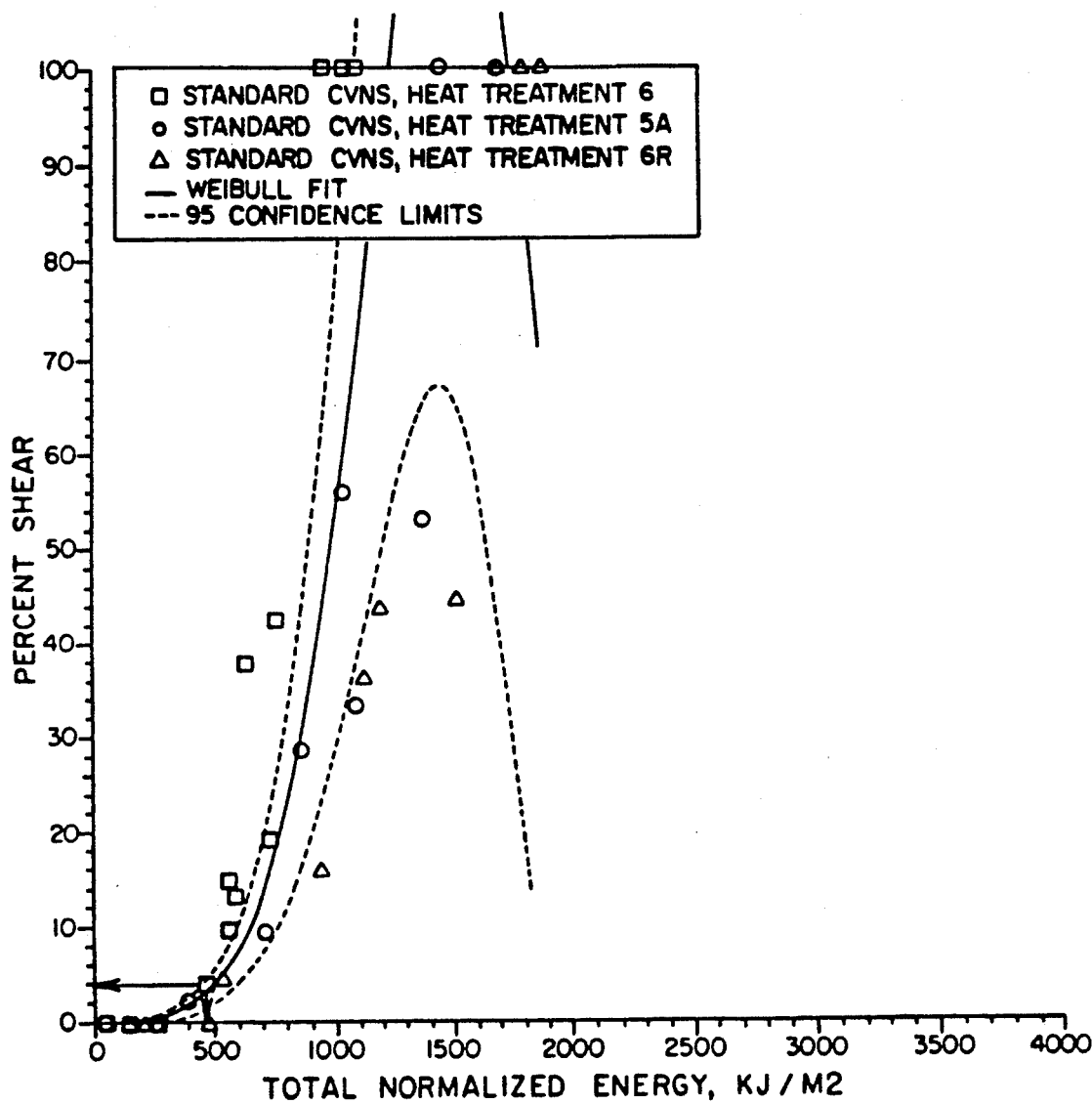
FIG. 15 is a graph of the normalized total energy vs percent shear as fracture transition criteria for Charpy specimens showing three materials that were tested.
Figure 16:
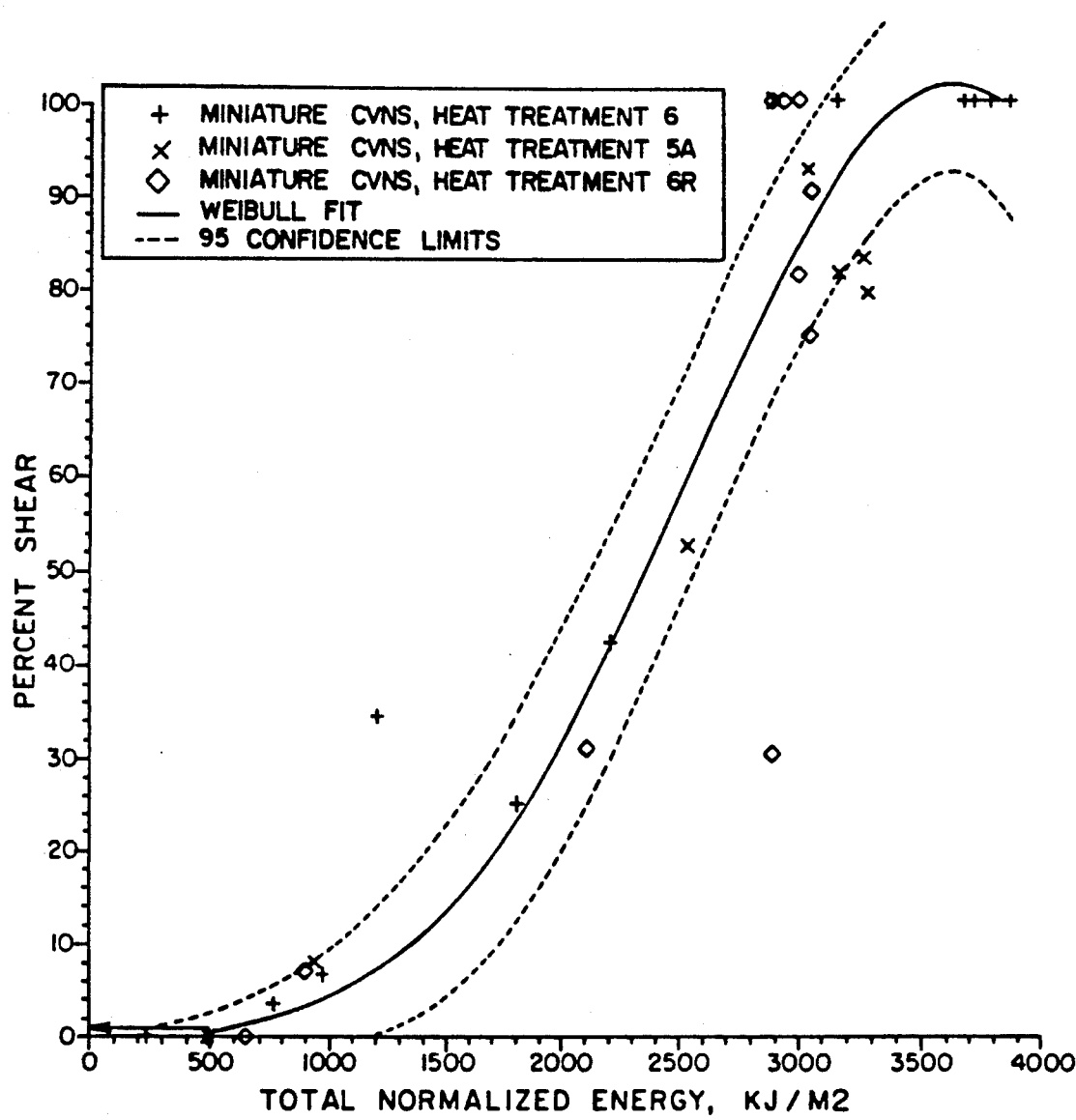
FIG. 16 is a graph of the normalized total energy vs percent shear as fracture transition criteria showing curves for three materials that were tested with miniature specimens.

The normalized energy data and the fracture appearance data were fit and the results are shown in FIGS. 15 and 16. It is possible to plot a single curve with reasonable accuracy for the standard or the miniature specimens for all 3 materials. However, it is obvious that the curves for the two specimen types are not coincident for both the energy and normalized energy parameters. When the 512 kJ/m$^2$ index is used to compare the fracture appearance for both sizes of specimens based on the normalized energy parameter, it is apparent that 512 kJ/m$^2$ corresponds to approximately 4 percent shear fracture appearance for the standard specimens, but to about 1 percent shear for the miniature specimens.

Figure 17:
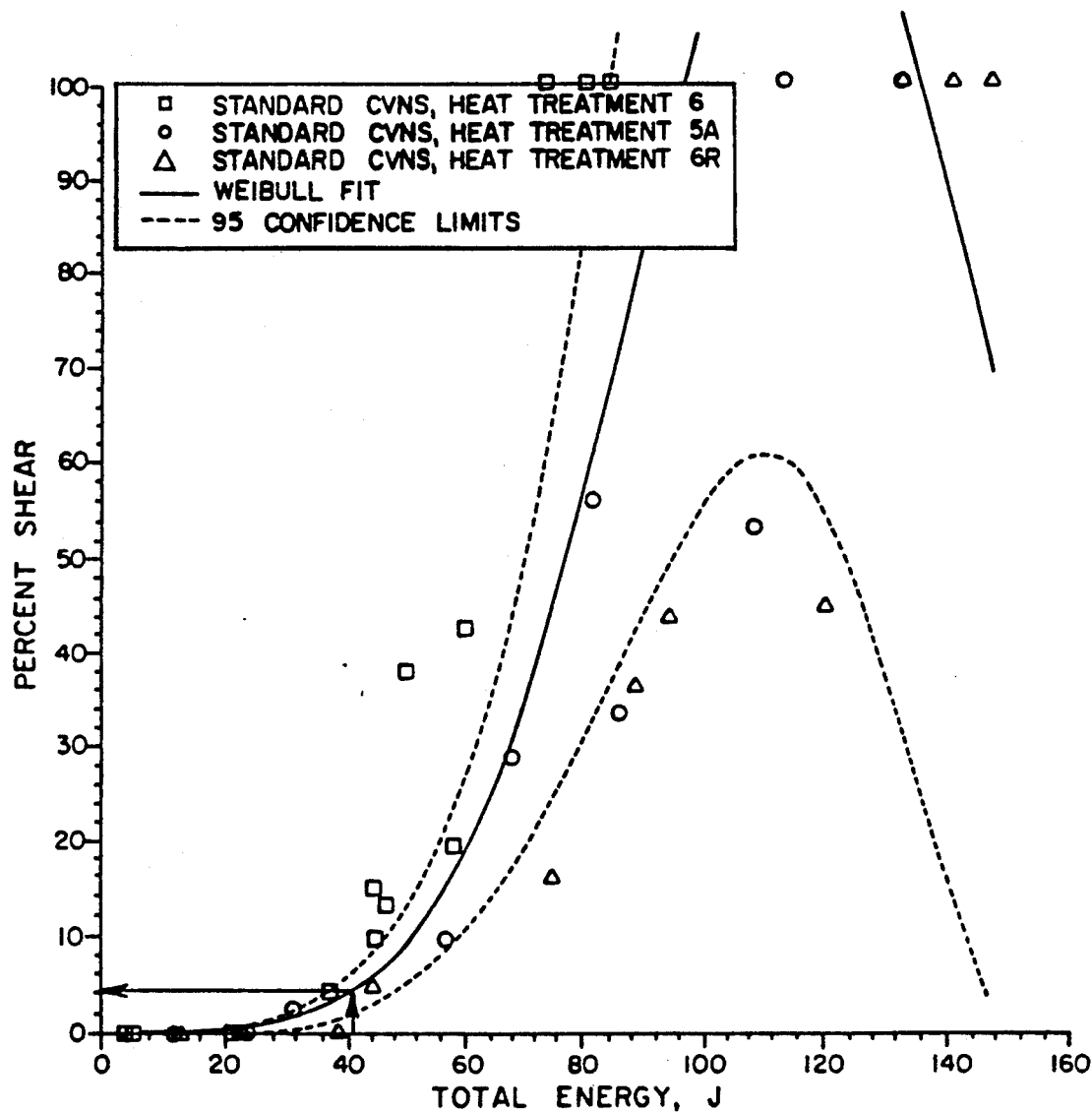
FIG. 17 is a graph of a non-normalized total energy vs percent shear as fracture transition criteria showing curves for three materials that were tested with ASTM standard Charpy specimens.
Figure 18:
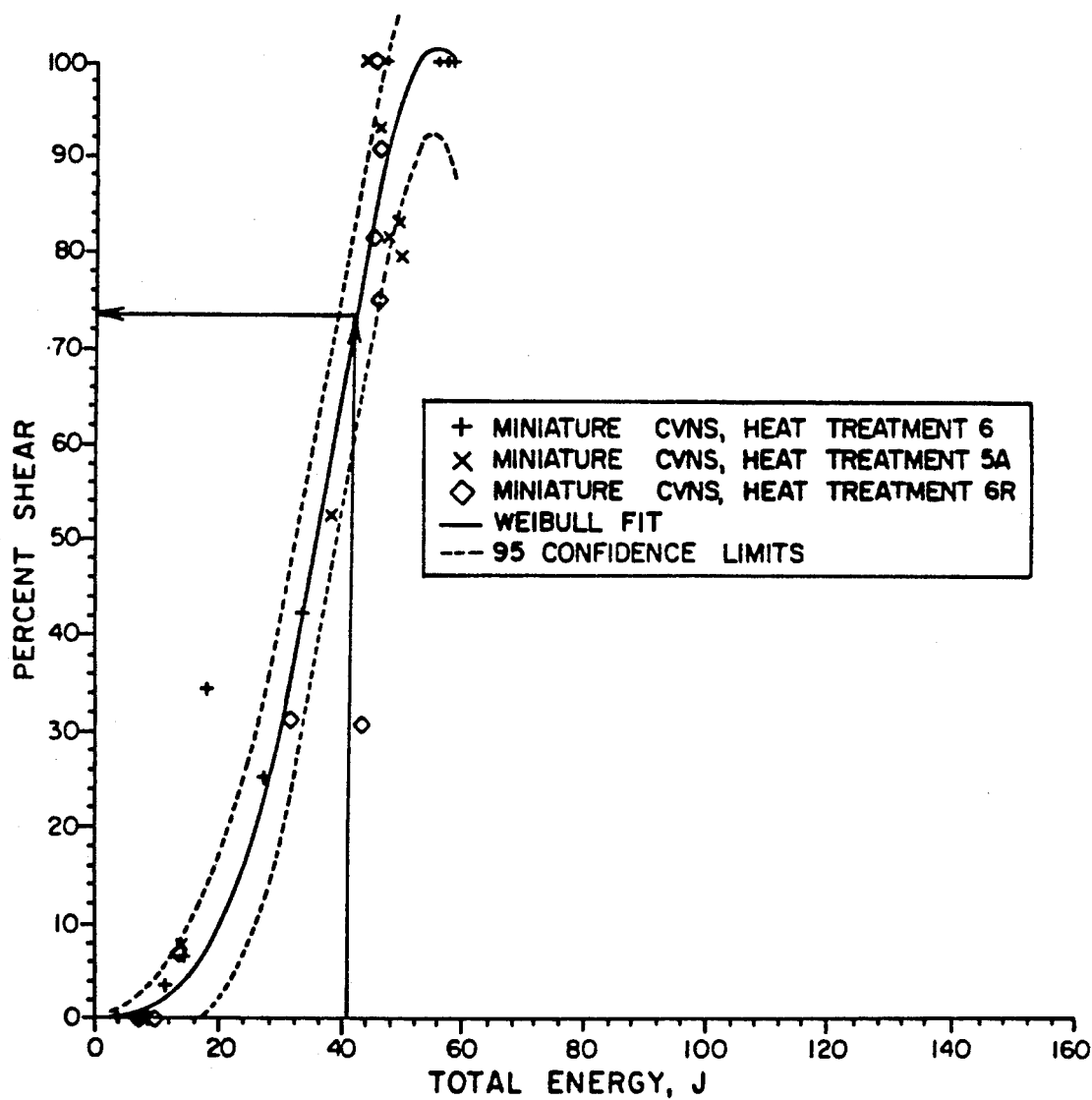
FIG. 18 is a graph of the non-normalized total energy vs percent shear as fracture transition criteria showing curves for three materials that were tested with miniature specimens.

If total absorbed energy is compared in this way to fracture appearance, the disparity between the miniature and standard specimens is even greater as shown in FIGS. 17 and 18. The miniature specimens at 41 J correspond to more than 70 percent shear, compared to about 4 percent for the standard specimens. The relative positions of the curves for standard and miniature specimens are now interchanged. It can be seem from a comparison of FIGS. 17 and 18 that the miniature specimens require less total energy to achieve a given value of a percent shear than the conventional CVNs. However, when the normalized energy is used, it is apparent that the miniature specimens seem to require more energy per unit fracture surface area to achieve a given level of percent shear than do the conventional CVNs. This observation suggests that the reasonable results obtained from the area normalization could be fortuitous, and may not hold for other materials.

These observations lead to the conclusion that using normalized energy as a Charpy parameter and 512 kJ/m$^2$ as a Charpy index for miniature specimens is probably not generally applicable. The reasonable data obtained may be attributed to the fortuitously small difference in fracture appearance between standard and miniature specimens at the 512 kJ/m$^2$ level, as is seen in FIGS. 15 and 16. Therefore, it is necessary to establish a new Charpy parameter (other than fracture appearance) and an appropriate index that could be used to correlate miniature with large specimen energy vs temperature data.

TABLE IV.2

% SHEAR FRACTURE APPEARANCE COMPARED TO ENERGY (FROM FIGURES IV.1 THRU IV.4)

|  | % Shear F.A. @ 512 kJ/m$^2$ | % Shear F.A @ 41 J |
| --- | --- | --- |
| Standard Specimens[1] | 4% | 4% |
| Miniature Specimens[1] | 1% | 70% |

[1](All 3 Materials)

While fracture appearance can serve as a Charpy parameter for any specimen size, its measurement is tedious and often not consistent with the requirements of current regulations. A new FMTB parameter and an appropriate index which makes use of load-deflection curves has been found. Besides being less tedious to measure than fracture appearance, the parameter obtained from the load-deflection traces is more amenable to automated or computerized data acquisition techniques.

It is well established that the total energy absorbed in fracturing a specimen can be partitioned into pre-maximum and post-maximum load energies. The energy prior to maximum load can be portioned into:

(1) elastic stored energy
(2) crack formation energy, and
(3) plastic deformation energy.

The miniature specimen differs from the conventional one in size and in geometry. Since the miniature specimen has a different span-to-width ratio, different anvil and punch geometry, and also has side grooves, the crack initiation energy and its ratio to total energy is different in the two specimen types, and therefore not a useful index.

The post-maximum load energy can be partitioned into:

(1) elastic stored energy
(2) plastic deformation energy, and
(3) stable crack propagation energy.

The elastic energy is available to drive the cleavage fracture. The remaining post-maximum load energy is associated with the plastic deformation work and work that goes into propagating a stable crack. Therefore, the post-maximum load energy is less sensitive to differences in specimen geometry and correlates well with fracture appearance, i.e., percent shear. The onset of the maximum load corresponds approximately to crack initiation. This assumption is a reasonable one for some materials and test temperatures. It is possible to measure crack formation using EP techniques.

Figure 19:
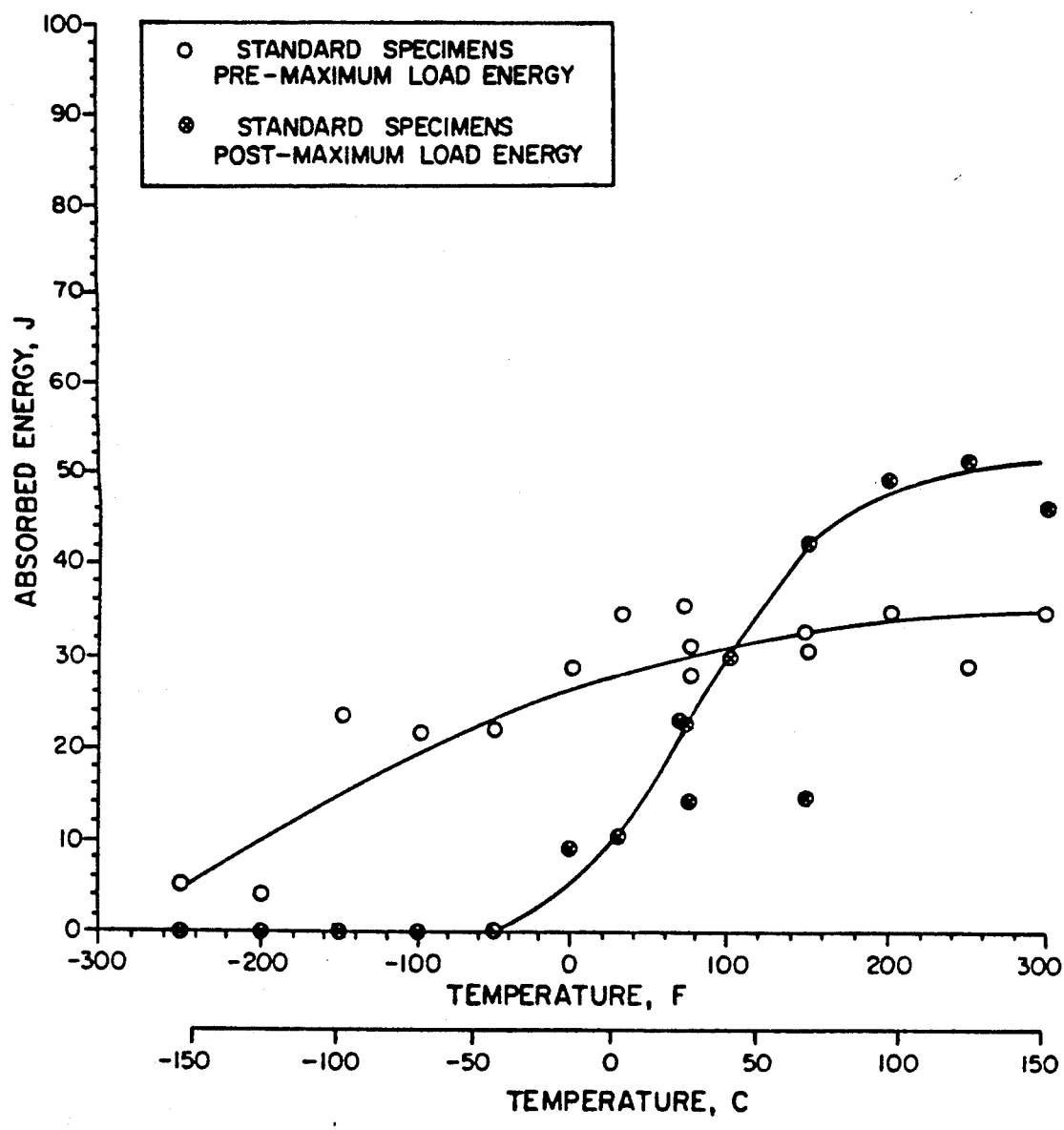
FIG. 19 is a graph of the pre-maximum and post-maximum load energies vs temperature for ASTM standard specimens.
Figure 20:
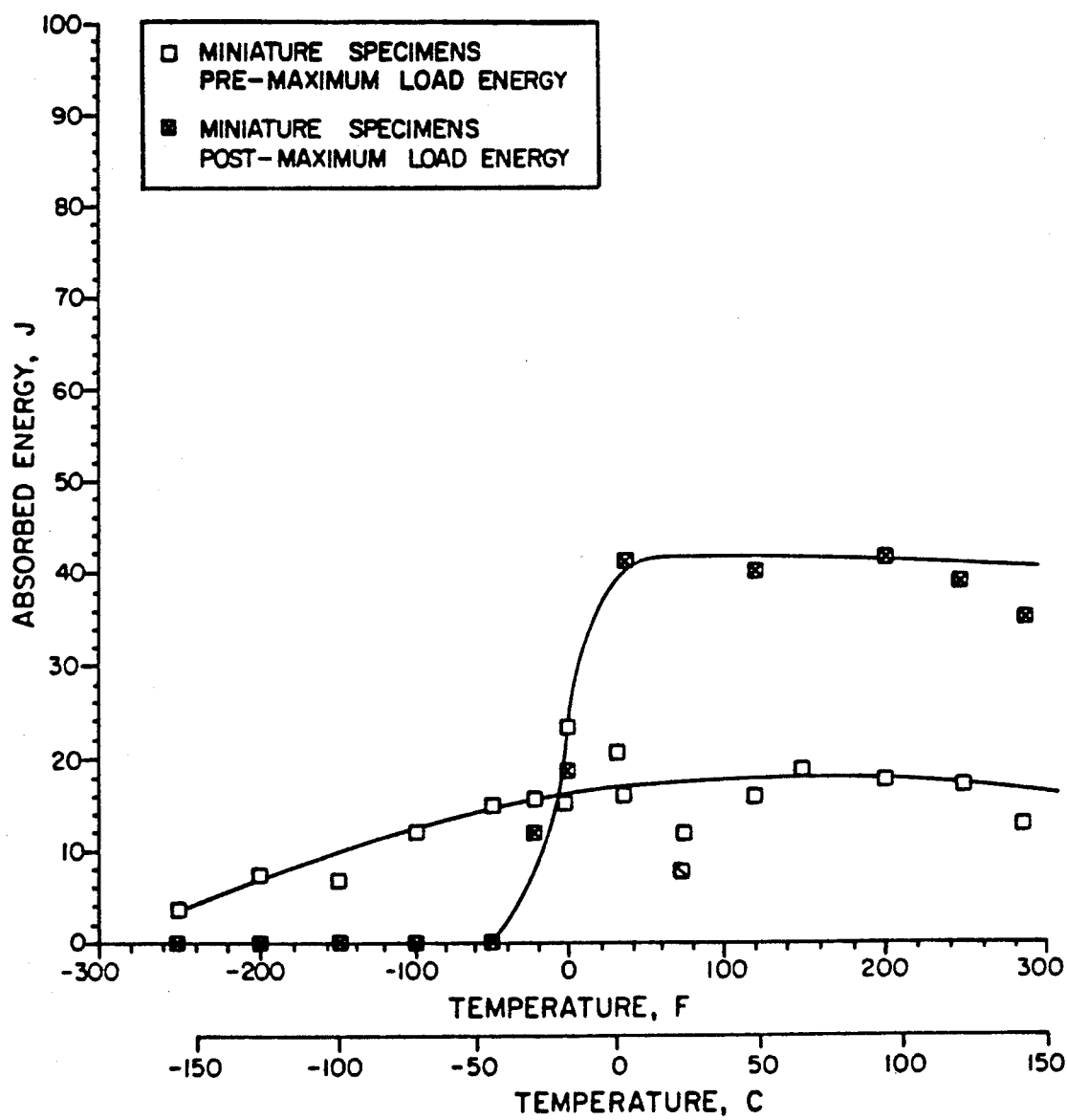
FIG. 20 is a graph of the pre-maximum and post-maximum load energies vs temperature for miniature FMTB specimens.

By partitioning the total energy into pre-maximum and post-maximum load energies, and plotting these versus testing temperature, it can be shown, that the pre-maximum load energy does not show a conspicuous transition in fracture behavior. As stated earlier, pre-maximum load energy is associated with elastic stored energy, crack initiation and plastic deformation near the notch. On the other hand, the post-maximum load energy exhibits a distinct transition. FIGS. 19 and 20 illustrate this behavior for the 60OR-93 material.

Crack initiation can be defined as the complete formation of a full-width crack across the length of the notch defined here, is complete when maximum load is reached, the post-maximum load energy should be proportional to percent shear for a given specimen size and shape regardless of material. Therefore the post-maximum load energy can be used as a parameter for ductile fracture transition characterization. The differences in specimen size would result in the absolute values of post-maximum load energy being different between specimen types. However, the relative proportion of the energy that goes into crack propagation and plastic deformation correlate with fracture appearance for specimens of different sizes and shapes. It is necessary, therefore, to convert the absolute values of post-maximum load energy to percentages, by dividing by the total energy. The total energy used in the calculations can be defined as the sum of the absorbed energy up to the onset of cleavage or the energy absorbed in the formation of shear lips can be included or any other convenient energy measure. A plot of percent shear fracture appearance versus percent post-maximum load energy is given in FIG. 21. This figure shows that the data for all 3 materials in both specimen geometries can be fit by the same curve with reasonable accuracy. This curve demonstrates that the new FMTB parameter, percent post-maximum energy, can correlate miniature and large specimen data. A correlation of this kind now allows for the use of two criteria, one based on energy, and the other on fracture appearance.

Figure 21:
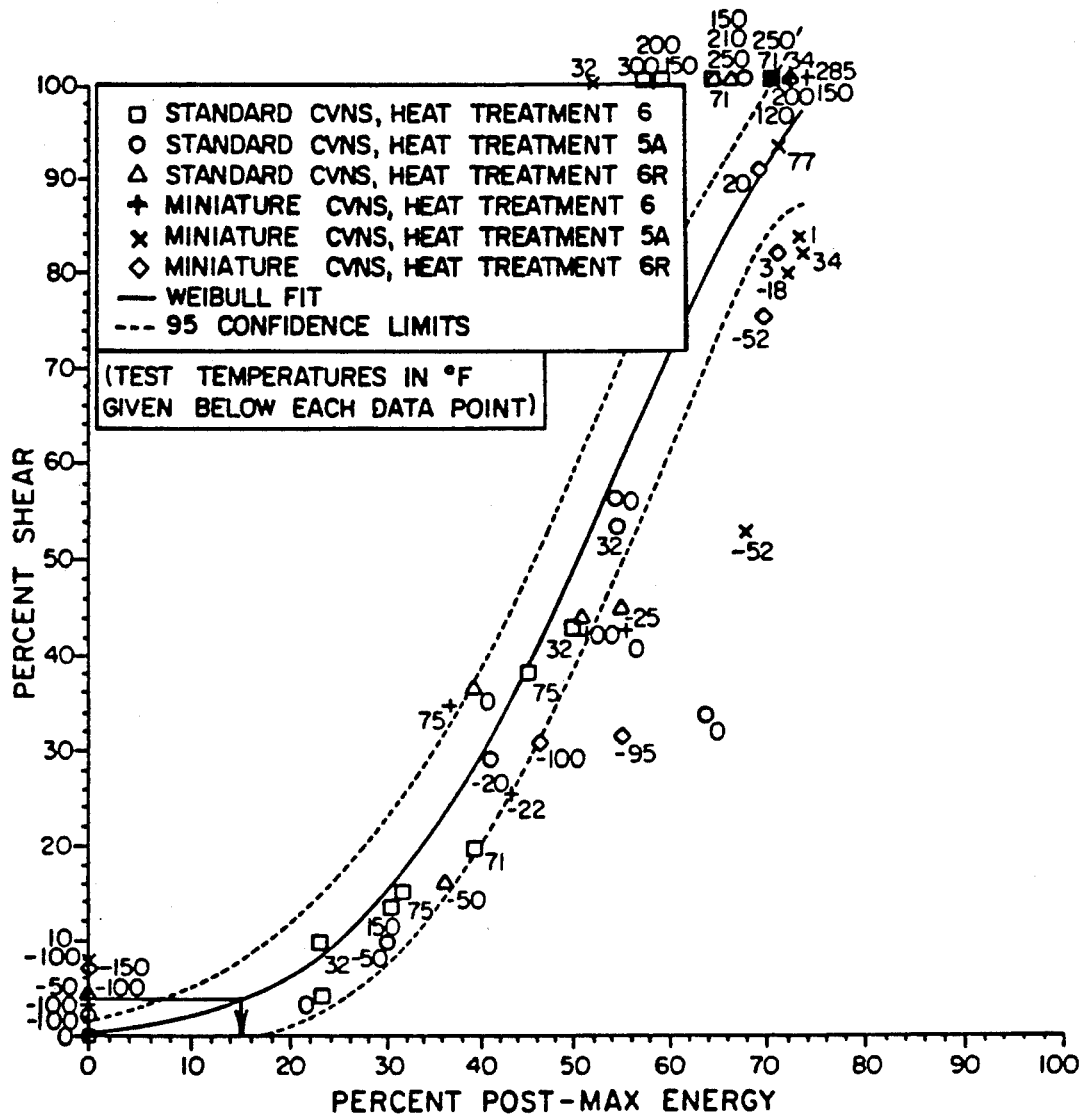
FIG. 21 is a graph showing correlation of percent of post-maximum load energy as a fracture transition criterion with percent shear for both ASTM standard and miniature FMTB specimens.
Figure 22:
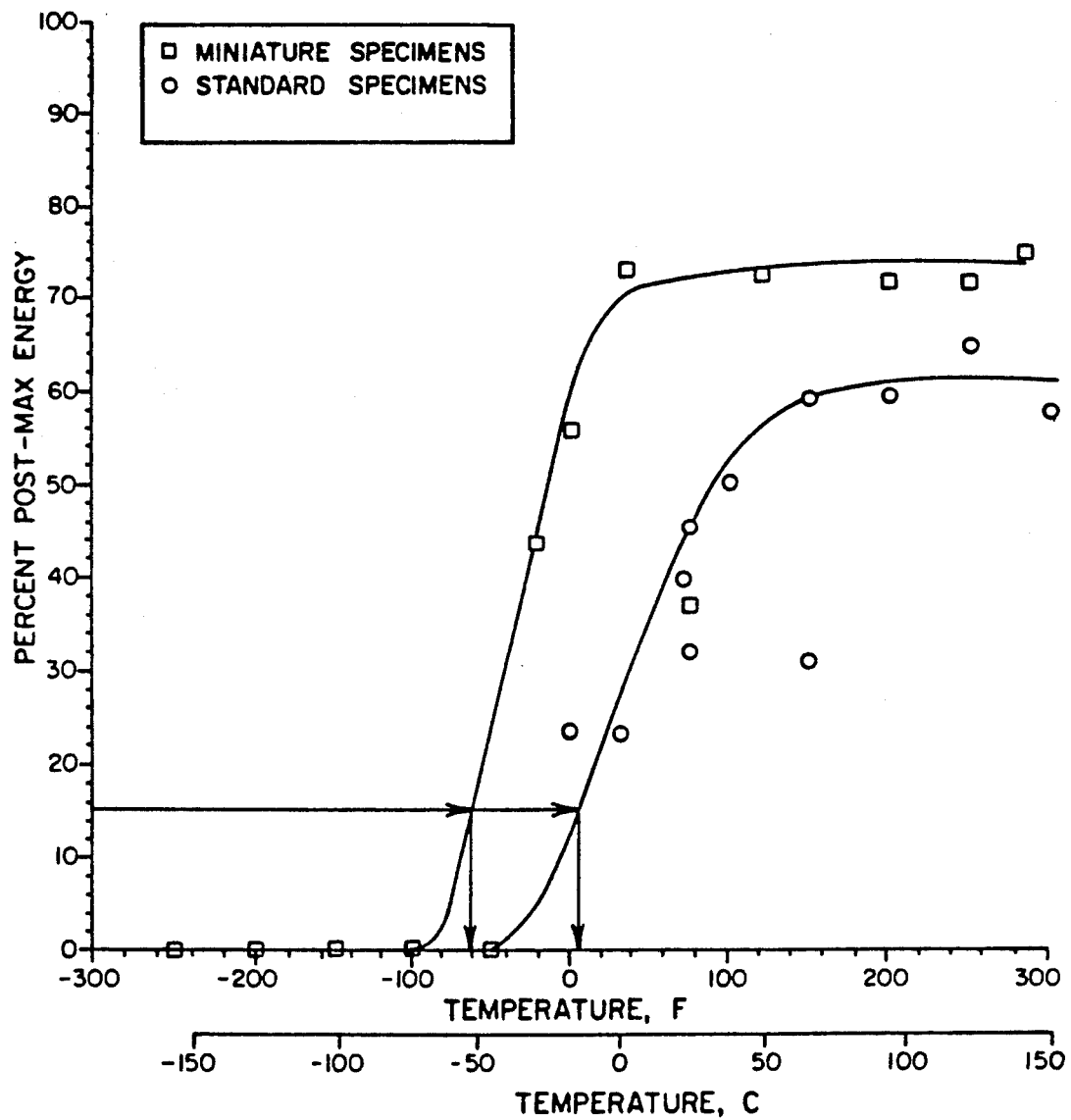
FIG. 22 is a graph showing material comparisons of transition temperature using the 15% post-maximum load energy index having both ASTM standard and miniature FMTB specimens plotted as temperature vs percent post-maximum energy for one of the test materials.
Figure 23:
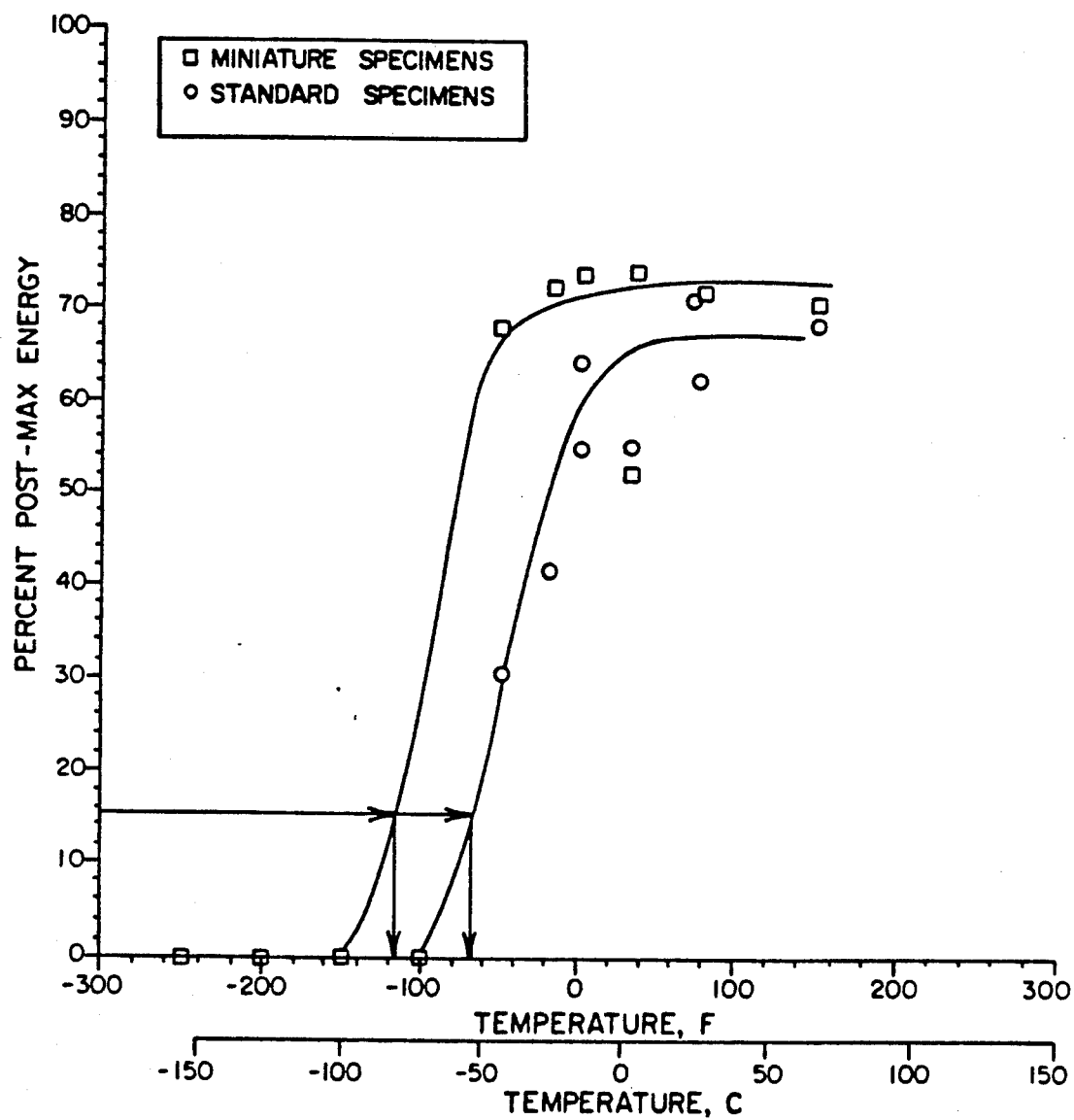
FIG. 23 is a graph showing material comparisons of transition temperature using the 15% post-maximum load energy index having both ASTM standard and miniature FMTB specimens plotted as temperature vs percent post-maximum energy for another of the test materials.
Figure 24:
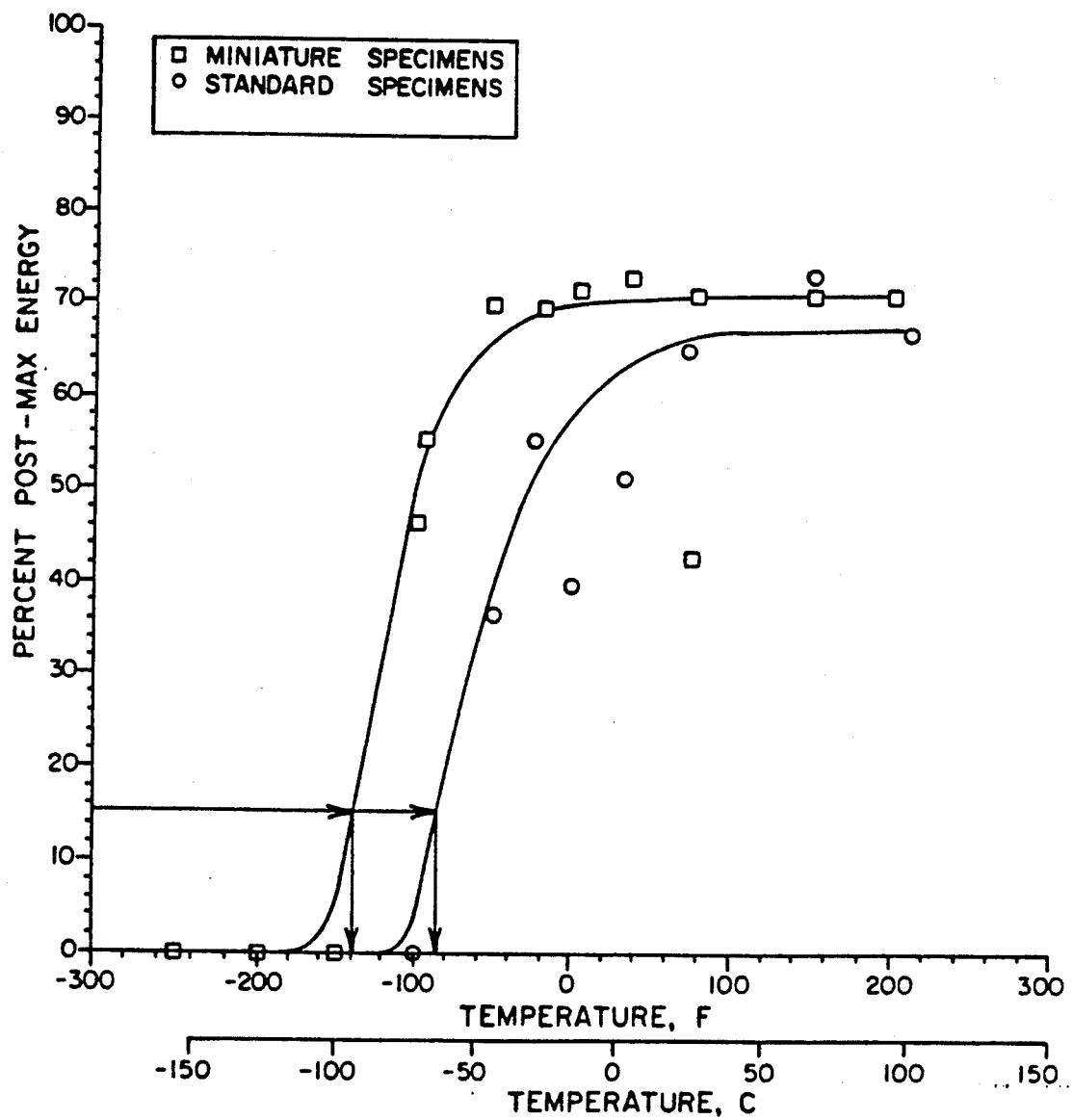
FIG. 24 is a graph showing material comparisons of transition temperature using the 15% post-maximum load energy index having both ASTM standard and miniature FMTB specimens plotted as temperature vs percent post-maximum energy for still another test material.
Figure 25:
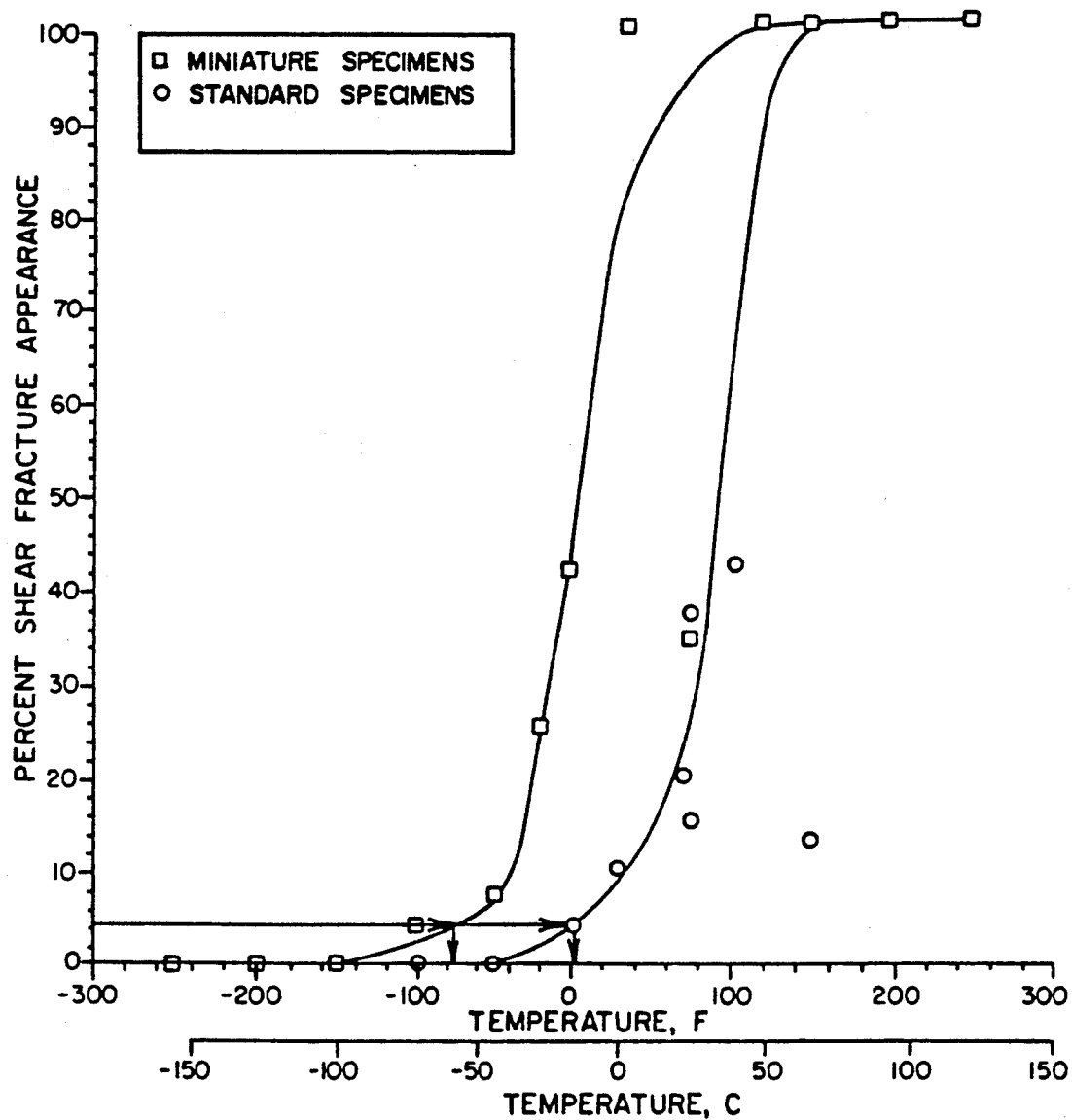
FIG. 25 is a graph showing transition temperature using the four percent shear fracture index showing both standard ASTM specimens and miniature FMTB specimens and plotted as temperature vs shear fracture appearance for the same material as FIGS. 20 and 22.
Figure 26:
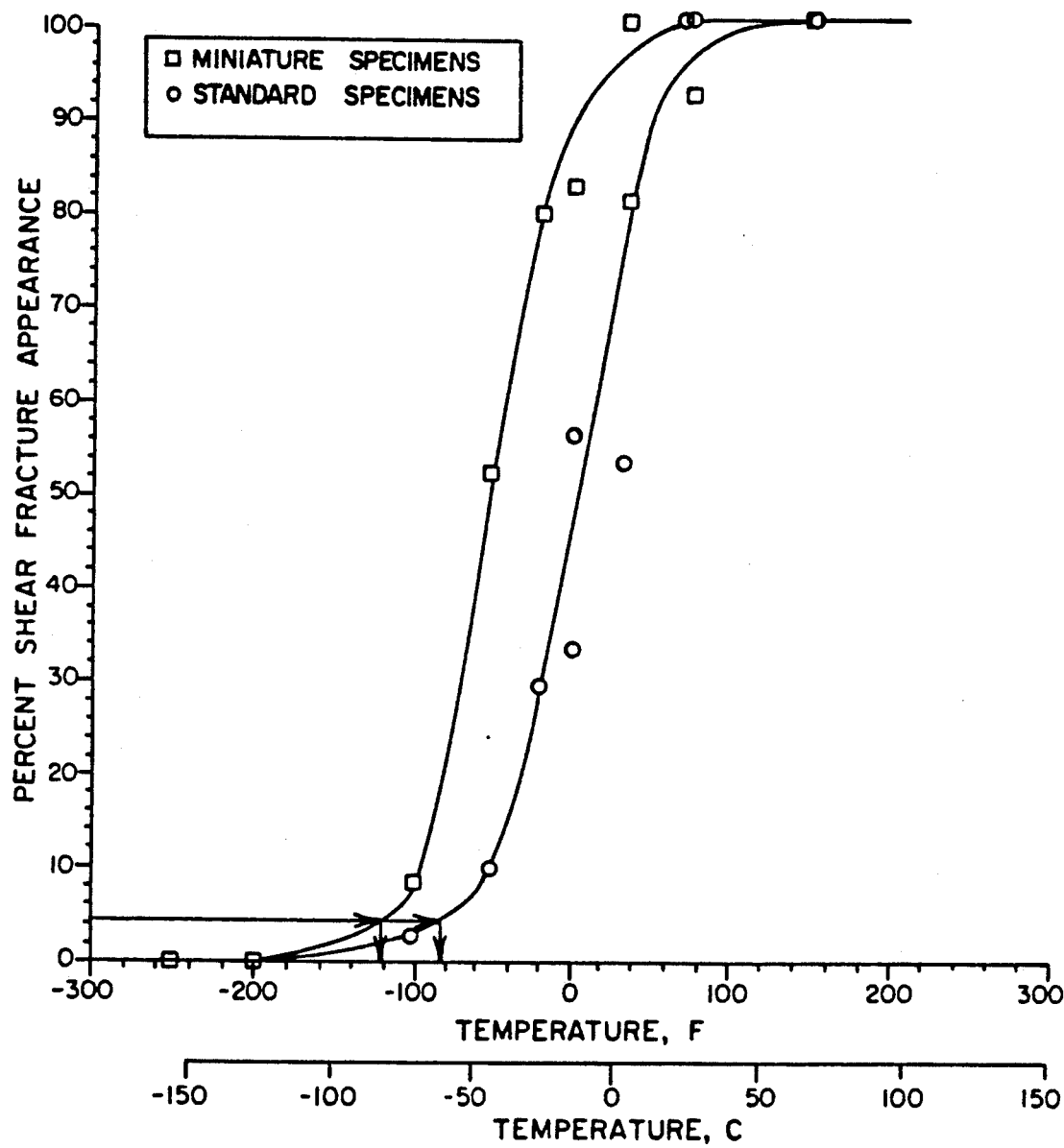
FIG. 26 is a graph showing transition temperature using the four percent shear fracture index showing both standard ASTM specimens and miniature FMTB specimens and plotted as temperature vs shear fracture appearance for the same material as FIG. 23.
Figure 27:
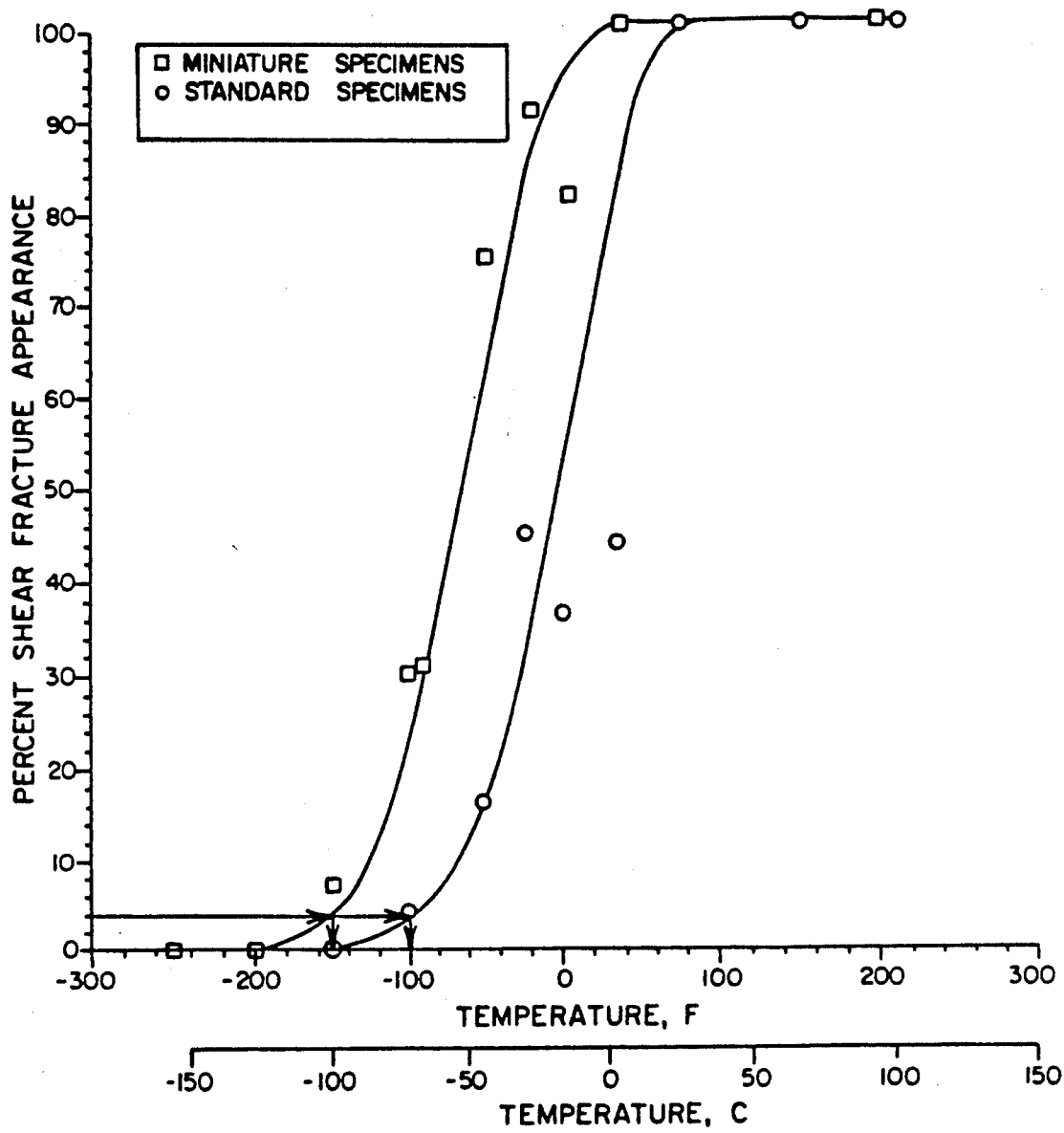
FIG. 27 is a graph showing transition temperature using the four percent shear fracture index showing both standard ASTM specimens and miniature FMTB specimens and plotted as temperature vs shear fracture appearance for the same material shown in FIG. 24.

FIG. 21 provides the correlation for obtaining indices for both specimen dimensions. The technique can be used to relate any specimen geometries which yield fracture transition data.

Thus, from FIG. 17 for the standard CVNs, a Charpy energy level of 41 Joules corresponds to approximately 4% shear fracture appearance. Referring to FIG. 21, this level of shear corresponds to about 15% post-maximum load energy. Thus when fracture appearance is used as the Charpy parameter, the corresponding index is 4% shear. When percent post-maximum load energy is chosen as the Charpy parameter, an index of 15% post-maximum load energy is used as the index.

Therefore, when the parameters of percent shear fracture appearance or percent post-maximum load energy are plotted versus test temperature (FIGS. 22 thru 27), transition temperatures for each material may be obtained at these new index levels (4% shear and 15% PME respectively). Table IV.3 summarizes these transition temperatures.

On comparing these transition temperatures with the standard CVN dynamic transition temperatures, the correction factors in the transition temperatures due to rate effect and size effect are obtained. Table IV.4 shows these values. The average shift due to rate effect is 49.3° C. (89.3° F.). The average shift due to size effect is 31.1° C. (56.0° F.).

Figure 28:
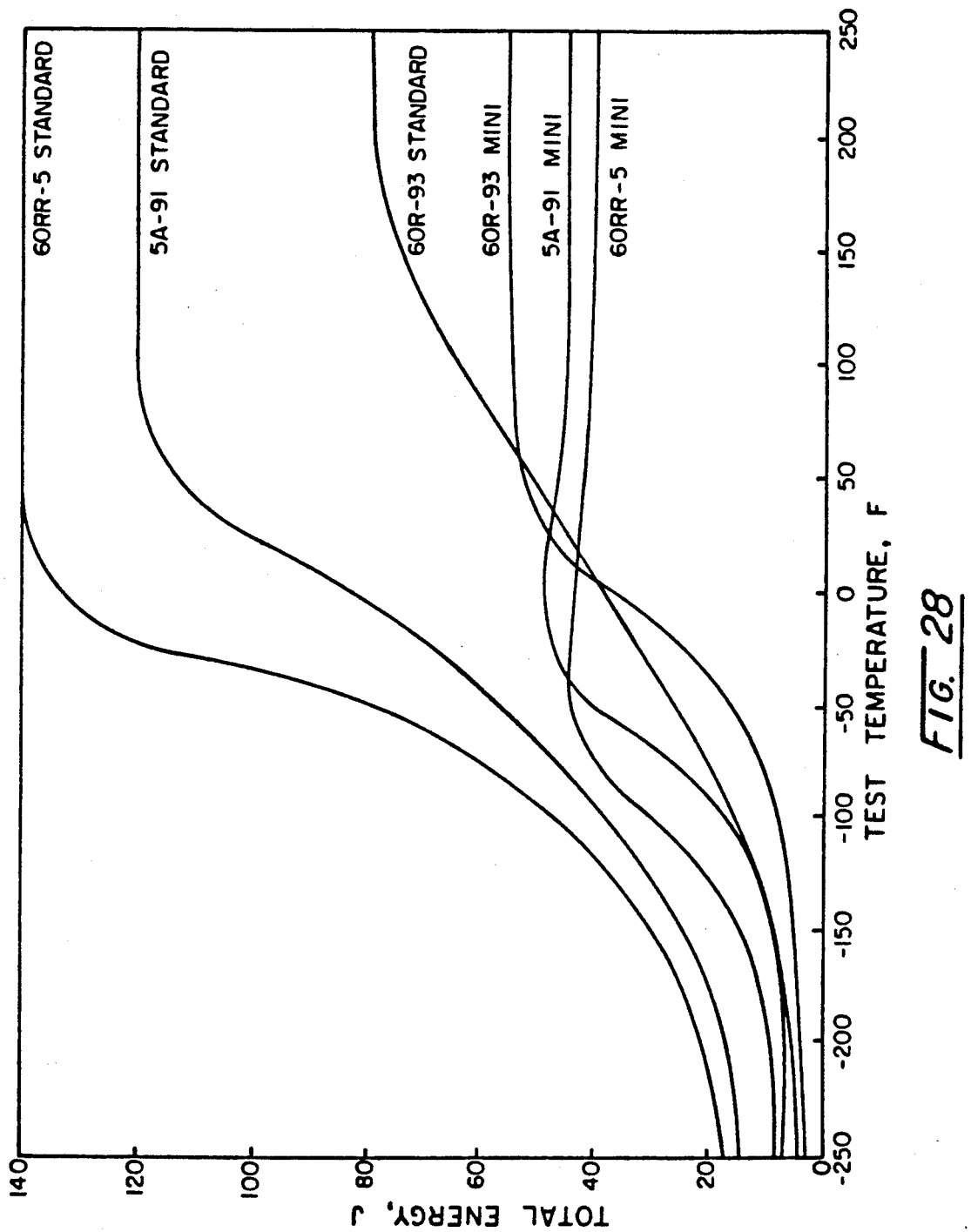
FIG. 28 is a graph showing a comparison of upper self energies for each of the test materials and each of the types of specimens plotted as test temperature vs total energy.

FIG. 28 shows plots of energy versus test temperature for the three material heats and both specimen sizes. Table IV.5 gives approximate values of the Upper Shelf Energy (USE) in terms of Joules, kJ/m$^2$, and also as the percent post-maximum load energy (100.0X.PME/TE).

TABLE IV.3

TRANSITION TEMPERATURES FROM % SHEAR AND FROM $\frac{\% \text{ P.M.E.}}{\text{T.E.}}$

| Material | 60R-93 | | 5A-91 | | 60RR-5 | |
|---|---|---|---|---|---|---|
| | Stand | Mini | Stand | Mini | Stand | Mini |
| 15% $\frac{\text{P.M.E.}}{\text{T.E.}}$ | −15 | −54 | −57 | −82 | −65 | −96 |
| 6% SHEAR | −18 | −59 | −62 | −84 | −73 | −101 |

TABLE IV.4

TRANSITION TEMPERATURE SHIFTS DUE TO RATE EFFECT AND SIZE EFFECT

| | Std Spec Impct TT [MANA85] 'C | Std Spec Slw Bnd TT 'C | Mni Spec Slw Bnd TT 'C | (Rate Effect) Stnd Spec Impct to Slw Bnd Shift 'C | (Size Eft) Stnd Slw Bend to Mni Slw Bend Shift 'C |
|---|---|---|---|---|---|
| 60R-93 | 40 | −16 | −57 | 56 | 41 |
| 5A-91 | −7 | −59 | −53 | 44 | 26 |
| 60RR-5 | −29 | −69 | −98 | 60 | 29 |

Average Rate Effect Shift: 49.3 C (89.3 F.) O-C
Average Size Effect Shift: 31.1 C (56.0 F.)

TABLE IV.5

| Material | UPPER SHELF ENERGY | | |
|---|---|---|---|
| | Joules | kJ/m$^2$ | % PME/TE |
| UPPER SHELF ENERGY [USE] FOR STANDARD SPECIMENS | | | |
| 60R-93 | 80 | 1000 | 60% |
| 5A-91 | 120 | 1500 | 69% |
| 60RR-5 | 140 | 1750 | 69% |
| UPPER SHELF [USE] | | | |

TABLE IV.5-continued

| Material | UPPER SHELF ENERGY | | |
|---|---|---|---|
| | Joules | kJ/m$^2$ | % PME/TE |
| FOR MINIATURE SPECIMENS | | | |
| 60R-93 | 55 | 3690 | 72% |
| 5A-91 | 45 | 3020 | 71% |
| 60RR-5 | 40 | 2750 | 70% |

FIG. 28 and Table IV.5 show that with respect to USE, the miniature specimen tests do not evaluate the 3 material heats in the same order as do the conventional CVN tests. According to the conventional CVN tests, the Upper Shelf Energy shows increases from the most brittle material (60R-93) to the most ductile (60RR-5). This is the case whether the USE is measured in terms of Joules, kJ/m$^2$, or % PME/TE. However, in the miniature CVN tests, there is a decrease in the value of USE from 60R-93 material to 60RR-5. As anticipated, % PME/TE does not show differences between materials in the upper shelf region for either specimen size.

A general procedure for using miniature specimens to predict the shift in Charpy transition temperature for each class of steel may be summarized as follows:

1. Perform dynamic or slow-bend tests to fracture on both the standard and the miniature specimens. Choose the temperature range of testing to ensure data are obtained over the ductile-to-brittle transition.
2. Obtain for each specimen, as a function of test temperature, the following data:
   (a) Fracture Appearance, as the percentage of the total fracture surface area (excluding shear lips).
   (b) Total Energy absorbed to cleavage fracture, in kJ/m2 or Joules
   (c) The Post-Maximum Load Energy to cleavage fracture, in kJ/m2 or Joules.
   (d) The fractional Post-Maximum Load Energy, obtained by dividing the post-maximum load energy [from (c)] by the total energy [from (b)].
3. Plot Fracture Appearance versus Total Energy for the standard specimens.
4. Obtain the value of Fracture Appearance (as a percent of shear) corresponding to the 41 J or (or 512 kJ/m2) standard used in the nuclear industry.
5. Plot Fracture Appearance versus fractional Post-Maximum Load Energy for all the specimens, both miniature and standard CVN. Fit the data to a single curve.
6. From the value of Fracture Appearance obtained in 4, and the curve obtained in 5, get a value of Fractional Post-Maximum Energy. This value then corresponds to the 41 J standard.
7. From the graphs obtained in 2(a) and 2(d), use these values of Fracture Appearance and Fractional Post-Maximum Energy to get Transition Temperature for both the standard as well as the miniature specimens.

8. The difference between the two transition temperatures is the miniature specimen correction factor.

9. A further correction factor in the transition temperature for a given specimen size is due to the effect of strain-rate. (Strain-rate sensitive steels will exhibit a translation in Charpy transition temperature depending on whether the tests are performed at impact or slow-bend rates.) If this translation due to strain-rate effect is known for the steel under investigation, the Charpy impact transition temperature may be obtained from the slow-bend transition temperature by simple addition.

It is herein understood that although the present invention has been specifically disclosed with the preferred embodiment and examples, modification and variation of the concepts herein disclosed may be resorted to by those skilled in the art. Such modifications and variations are considered to be within the scope of the invention and the appended claims.

The following references are incorporated herein:

(1) Brown, W. F., Jr. Lubahn, J. D., and Ebert, L. J., "Effects of Section Size on the Static Notch Bar Tensile Properties of Mild Steel Plate", The Welding journal, Research Supplement, 554-s to 559-s (October 1947).

(2) Buffum, D. C., "Investigation of Square Sub-Sized V-Notched Charpy Specimens", ASTM Bulletin (TP 143), 45–47 (September 1949).

(3) Corwin, W. R., and Hoagland, A. M., "Effect of Specimen Size and Material Condition on the charpy Impact Properties of 9CR-1Mo-V-Mb Steel", in *The Use of Small Scale Specimens for Testing Irradiated Material*", ASTM STP No. 888, 325–338 (1986).

(4) Davidenkov, N., Shevandin, C., and Wittman, F., "The Influence of Size on the Brittle Strength of Steel", Transactions ASME, Vol. 69, 63 (1947)

(5) Grounes, M., "Review of Swedish Work on Irradiation Effects in Pressure Vessel Steels and on Significance of Data Obtained", in *Effects of Radiation on Structural Metals*, ASTM STP No. 426, 224–259 (1967).

(6) Jonassen, F., "Discussion on Effects of Section Size on the Static Notch Bar Tensile Properties of Mild Steel Plate", The Welding Journal, Research Supplement, 27-s (January 1948).

(7) Lucas, G. E., Odette, G. R., Sheckherd, J. W., McConnell, P., and Perrin, J., "Subsized Bend and Charpy V-Notch Specimens for Irradiated Testing", in *The Use of Small Scale Specimens for Testing Irradiated Material*", ASTM (STP No. 888, 305–324 (1986).

(8) Macgregor, C. W., and Grossman, N., "Dimensional Effects in Fracture", The Welding Journal, Research Supplement, 20-s to 26-s (January 1952).

(9) Orner, G. N., and Hartbower, C. E., "Effect of Specimen Geometry on Charpy Low-Blow Transition Temperature", The Welding Journal, Research Supplement, 521-s to 527-s (December 1957).

(10) Schwartzbart, H., and Sheehan, J. P., "Effect of specimen Size on Notched Bar Impact Properties of Quenched and Tempered Steels", ASTM Proceedings, Vol. 54, 939–955 (1954).

(11) Wilsin, W. M., Hechtman, R. A., and Bruckner, W. H., "Cleavage Fracture of Ship Plates as Influenced by Size Effect", The Welding Journal, Research Supplement, 200-s to 208-s (April 1948).

I claim:

1. A process of determining the fracture mode transition behavior (FMTB) of solid materials, by loading the material, comprising:
    (a) providing a specimen with a side element, and having a volume and smallest dimension sufficient to establish continuum behavior in all directions, and with a volume not more than $10^7$ times said sufficient volume, said specimen having a notch and/or crack on the side element;
    (b) modifying the stress field of the specimen by providing at least one groove on the side element juxtaposed to the notch and/or crack to provide overlapping stress field that include transverse stress components which are approximately equal throughout the thickness of the side with the notch, when the specimen is loaded, resulting in measurable FMTB;
    (c) deforming the specimen by applying a load on the specimen in a direction different than the orientation of the modified stress field;
    (d) measuring at least one key variable in step c; and
    (e) determining the FMTB of the material from the measurements taken according to the principles of the finite element method and/or the principles of linear or nonlinear material mechanics.

2. A process according to claim 1 wherein the volume of the specimen is approximately one twentieth or less than the volume of the standard ASTM specified specimen.

3. A process, according to claim 1 wherein the specimen is in the shape of a cylinder.

4. A process according to claim 1 wherein the specimen is solid and of three dimensional rectangular shape, having three pairs of parallel sides including two pairs of elongate sides and one pair of smaller ends, with the notch on one of the elongate sides and the grooves are in both of the elongate sides which abut the side with the notch.

5. A method according to claim 4 wherein the grooves intersect the notch.

6. A process according to claim 1 wherein the specimen is in the shape of a trapezoid.

7. A process of determining the fracture mode transition behavior (FMTB) of solid material, by loading the material, comprising:
    (a) providing a miniature specimen, having a plurality of sides and ends, of material having a volume and smallest dimension sufficient to establish continuum behavior in all directions, and with a volume not more than $10^7$ times said sufficient volume, said specimen having a notch intermediate the ends on one side;
    (b) modifying the stress field of the specimen by providing grooves on two sides opposite to the notch at a position intersecting the notch, so as to induce stress in the specimen in a pre-selected field of orientation in the notch;
    (c) deforming the specimen by applying a load on the specimen in a direction different than the orientation of the modified stress field;
    (d) measuring at least one key variable in step c; and
    (e) determining the FMTB of the material from the measurements taken according to the principles of the finite element method and/or the principles of linear or nonlinear material mechanics.

8. A process of determining the ductile-brittle transition temperature (DBTT) of solid materials, by loading the material comprising:
  (a) providing a specimen, having a plurality of sides and ends, of the material having a volume and smallest dimension sufficient to establish continuum behavior in all directions, and with a volume not more than $10^7$ times said sufficient volume, said specimen having a notch and/or crack intermediate the ends on one side;
  (b) modifying the stress field of the specimen by providing grooves on the two sides opposite to the notch and or cracks to provide overlapping stress field that include transverse stress components which are approximately equal throughout the thickness of the side with the notch, resulting in a measurable DBTT;
  (c) deforming the specimen by applying a load on the specimen in a direction different than the orientation of the modified stress field;
  (d) measuring at least one key variable in step c; and
  (e) determining the DBTT of the material from the measurements taken according to the principles of the finite element method and/or the principles of linear or nonlinear material mechanics.

9. A process according to claim 8 wherein the volume of the specimen is approximately one twentieth or less than the volume of the standard ASTM specified specimen.

10. A process according to claim 8 wherein the specimen is solid and of three dimensional rectangular shape, having three pairs of parallel sides including two pairs of elongate sides and one pair of smaller ends, with the notch on one of the elongate sides and the grooves are in both of the elongate sides which abut the side with the notch.

11. A method according to claim 10 wherein the grooves intersect the notch.

12. A process of determining the ductile-brittle transition temperature (DBTT) of solid material, comprising:
  (a) providing a miniature specimen, having a plurality of sides and ends, of the material having a volume and smallest dimension sufficient to establish continuum behavior in all direction, and with a volume not more than $10^7$ times said sufficient volume, said specimen having a notch and/or crack intermediate the ends on one side;
  (b) modifying the stress field of the specimen by providing grooves on the two sides opposite to the notch at a position intersecting the notch, and/or crack so as to induce stress in the specimen in a preselected field of orientation in the notch;
  (c) deforming the specimen by applying a load on the specimen in a direction different than the orientation of the modified stress field;
  (d) measuring at least one key variable in step c; and
  (e) determining the DBTT of the material from the measurements taken according to the principles of the finite element method and/or the principles of linear or nonlinear material mechanics.

13. A specimen of solid material having a volume and smallest dimension sufficient to establish continuum behavior in all directions, with a volume of not more than $10^7$ times said sufficient volume; said specimen being constructed as an elongated beam-like shape including three pairs of parallel sides and having a notch intermediate the ends and on one elongated side, with the notch protruding into each of the contiguous opposing elongated sides; and being further provided with grooves parallel in the sides abutting the side with the notch are with the grooves intersecting the notch.

14. A miniature specimen of solid material for determining the ductile-brittle transition temperature (DBTT) of the material having a volume and smallest dimension sufficient to establish continuum behavior in all directions, with a volume of not more than $10^7$ time said sufficient volume; said specimen being constructed as elongated beam-like shape including three pairs of parallel sides and having a notch intermediate at the ends and on one elongated side, with the notch protruding into each of the contiguous opposing elongated sides; and being further provided with grooves in the parallel sides abutting the side with the notch, with the grooves intersecting the notch; so that when tested by bending the side opposite to the notch, overlapping stress fields are induced in a plane juxtaposed to the plane intersecting the two grooves and the notch, and with the stress field having transverse stress components which are approximately equal throughout the thickness of the side with the notch, resulting in a measurable DBTT.

* * * * *